United States Patent
Hayes et al.

(10) Patent No.: US 10,179,938 B2
(45) Date of Patent: Jan. 15, 2019

(54) ARTIFICIAL SELECTION METHOD AND REAGENTS

(71) Applicant: Agriculture Victoria Services Pty Limited, Attwood (AU)

(72) Inventors: Ben Hayes, Kensington (AU); Michael Goddard, Diamond Creek (AU)

(73) Assignee: AGRICULTURE VICTORIA SERVICES PTY LIMITED, Attwood (AU)

(*) Notice: Subject to any disclaimer, the term of this patent is extended or adjusted under 35 U.S.C. 154(b) by 0 days.

(21) Appl. No.: 14/245,334

(22) Filed: Apr. 4, 2014

(65) Prior Publication Data

US 2014/0220575 A1  Aug. 7, 2014

Related U.S. Application Data

(63) Continuation of application No. 12/448,463, filed as application No. PCT/AU2007/002006 on Dec. 21, 2007.

(60) Provisional application No. 60/876,623, filed on Dec. 21, 2006.

(51) Int. Cl.
*C12Q 1/6888* (2018.01)
*C12Q 1/68* (2018.01)
*A01K 67/02* (2006.01)

(52) U.S. Cl.
CPC ............ *C12Q 1/6888* (2013.01); *A01K 67/02* (2013.01); *C12Q 1/68* (2013.01)

(58) Field of Classification Search
CPC ......... C12Q 1/68; C12Q 1/6888; A01K 67/02
See application file for complete search history.

(56) References Cited

U.S. PATENT DOCUMENTS

| | | | |
|---|---|---|---|
| 5,041,371 | A | 8/1991 | Cowan et al. |
| 5,374,523 | A | 12/1994 | Collier et al. |
| 5,614,364 | A | 3/1997 | Tuggle et al. |
| 6,492,142 | B2 | 12/2002 | Renaville et al. |
| 2007/0105107 | A1* | 5/2007 | Wang ................ A01K 67/02 435/6.11 |

FOREIGN PATENT DOCUMENTS

| | | |
|---|---|---|
| WO | WO 2002/036824 | 5/2002 |
| WO | WO 2003/004630 | 1/2003 |
| WO | WO 2003/104492 | 12/2003 |
| WO | WO 2004/048609 | 7/2004 |
| WO | WO 2004/083456 | 9/2004 |
| WO | WO 2005/056758 | 6/2005 |
| WO | WO 2005/078133 A2 | 8/2005 |
| WO | WO 2006/076573 | 7/2006 |
| WO | WO 2006/086846 A1 | 8/2006 |

OTHER PUBLICATIONS

Meuwissen The Et Al (2001) "Prediction of Total Genetic Value Using Genome-Wide Dense Marker Maps" Genetics Society of America, 157:1819-1829.

Emara and H Kim M G (2003) "Genetic Markers and their Application in Poultry Breeding" Poultry Science, 82:952-957.

Hayes Ben et al (2003) "Evaluation of marker assisted selection in pig enterprises" Livestock Production Science, 81:197-211.

Boichard D et al (1997) "The value of using probabilities of gene origin to measure genetic variability in a population" Genetics selection Evolution, 29:5-23.

Xiayi Ke and Lon R Cardon (2003) "Efficient selective screening of haplotype tag SNPs" Bioformatics Applications Note, 19:287-288.

Daniel O Stram "Tag SNP Selection for Association Studies" (2004) Genetic Epidemiology 27:365-374.

Paola Sebastiani et al (2003) "Minimal haplotype tagging" USA Issue 17:9900-9905.

Paul Scheet and Mattew Stephens "A Fast and Flexible Statistical Model for Large-Scale Population Genotype Data: Applications to Inferring Missing Genotypes and Haplotypic Phase" (2006) Genet, 78:629-644.

T. Li, J. Ding, GR Abecasis "Rapid Haplotype Reconstruction and Missing Genotype Inference" (2006) America Journal of Human Genetics, abstract only.

Pierre Nicolas, Fengzhu Sun and Lei M Li (2006) "A model-based approach to selection of tag SNPs" BMC Bioinformatics, 7:303-317.

Sharon R Browning "Multilocus Association Mapping Using Variable-Length Markov Chains" (2006) Am J. Hum Genet, 78:903-913.

Tier and Bunter "Estimating Genetic Merit When Genotype Data are Incomplete" (2003) Assoc. for the Adv of Animal Breeding and Genetics, 15:214-217.

Kinghorn "Use of segregation analysis to reduce genotyping costs" (1998) Journal of Animal Breeding and Genetics, 116:175-180.

Meuwissen "Determining Haplotypes and IBD-Probabilities From Densemarker Genotypes in Large Complex Pedigrees" (2006) Proceedings of 8th World Congress on Genetics Appl. to Livestock Production.

Macrossan at Al "Strategies for Cost Effective DNA Testing for the Thryoglobulin Gene in Beef Cattle" (2001) Proceedings of the Association for the Adv of Animal Breeding and Genetics, 14:309-312.

Bennewitz et al "Top down preselection using marker assisted estimates of breeding values in dairy cattle" (2004) Journal of Animal Breeding and Genetics, 121:307-318.

Henshall and Tier "An algorithm for sampling descent graphs in large complex pedigrees efficiently" (2003) Genetics Research, 81:205-212.

Van Arendonk et al "Use of Multiple Genetic Markers in Prediction of Breeding Values" (1991) Genetics, 137:319-329.

Goddard and Meuwissen "The Use of linkage disequilibrium to map quantitative trait loci" (2005) Australian Journal of Experimental Ag, 45:837-845.

Falconer and Mackay "Introduction to Quantitative Genetics" (1996) Longman, 76 pages.

Lynch and Walsh "Genetics and Analysis of Quantitative Traits" (1998) Sinauer Associates Inc, 97 pages.

(Continued)

*Primary Examiner* — Diana B Johannsen

(74) *Attorney, Agent, or Firm* — John P. White; Cooper & Dunham LLP

(57) ABSTRACT

The present invention provides methods for estimating the breeding value of individuals in populations such as those having small effective population size (Ne) e.g., to identify selection candidates having high breeding values, wherein the methods comprise inferring one or more genotypes for one or more markers at a locus or QTL to be the same as for an ancestor or founder or a subset of ancestors and/or founders from which a corresponding chromosome segment is derived and estimating the breeding value of the individual based on the inferred genotype(s).

16 Claims, No Drawings

(56) References Cited

OTHER PUBLICATIONS

Kearsey and Pooni "The Genetical Analysis of Quantitative Traits" (1996) Chapman & Hall, 56 pages.
Goddard (1998) "Gene Based Models for Genetic Evaluation—An Alternative to BLUP?" Proceedings of the 6th World Congress on Genetics Applied to Livestock Production, 33-36.
Fernando "Genetic Evaluation and Selection Using Genotypic, Phenotypic and Pedigree Information" (1998) Proceedings of the 6th World Congress on Genetics Applied to Livestock Production, 329-336.
Henshall and Goddard "Marker Assisted Selection in Complex Pedigrees Using Maximum Likelihood" (1998) Proceedings of the 6th World Congress on Genetics Applied to Livestock Production, 345-348.
Lee et al "Combining the Meiosis Gibbs Sampler With the Random Walk Approach for Linkage and Association Studies With a General Complex Pedigree and Multimarker Loci" (2005) Genetics, 171:2063-2072.
Bink and Van Arendonk "Detection of Quantitative Trait Loci in Outbred Populations With Incomplete Marker Data" (1999) Genetics, 151:409-420.
Bauer et al "Estimation of Breeding Values of Inbred Lines using Best Linear Unbiased Prediction (BLUP) and Genetic Similarities" (2006) Crop Science, 46:2685-2691.
Burdick et al "In silico method for inferring genotypes in pedigrees" (2006) Nature Genetics, 38(9):1002-1004.
Li and Jiang "Computing the Minimum Recombinant Haplotype Configuration from Incomplete Genotype Data on a Pedigree by Integer Linear Programming" (2005) Journal of Computational Biology, 12(6):719-739.
Abecasis et al "Merlin—rapid analysis of dense genetic maps using sparse gene flow trees" (2001) Nature Genetics, 30:97-101.
Fernando, Stricker and Elston "An efficient algorithm to compute the posterior genotypic distribution for every member of a pedigree without loops" (1993) Theor Appl Genet, 87:89-93.
Wright "Coefficients of Inbreeding and Relationship" (1922) The American Naturalist, 56:330-338.
Hazel "The Genetic Basis for Constructing Selection Indexes" (1943) Genetics, 28:476-490.
Henderson "Best Linear Unbiased Estimation and Prediction under a Selection Model" (1975) Biometrics, 31(2):423-417.
Henderson "A Simple Method for Computing the Inverse of a Numerator Relationship Matrix Used in Prediction of Breeding Values" (1976) Biometrics, 32(1):69-83.
Fernando and Grossman "Marker assisted selection using best linear unbiased prediction" (1989) Genet. Sel Evol. 21:467-477.
Nejati-Javaremi et al "Effect of total allelic relationship on accuracy of evaluation and response to selection" (1997) Journal of Anim. Sci, 75:1738-1745.
Sved JA "Linkage Disequilibrium and Homozygosity of Chromosome Segments in Finite Populations" (1971) Theoretical Population Biology, 2:125-141.
Stephens and Donnelly "A Comparison of Bayesian Methods for Haplotype Reconstruction from Population Genotype Data" (2003) Am. J. Hum. Genet. 73:1162-1169.
Matsuzaki "Genotyping over 100,000 SNPs in a pair of oligonucleotide arrays" (2004) Nature Methods, 1(2):109-111.
Carlson "Mapping complex disease loci in whole-genome association studies" (2004) Nature, 429:448-452.
Craig "Mapping complex disease loci in whole-genome association studies" (2005) Expert Rev. Mol. Diagn. 5:159-170.
Syvanen "Toward genome-wide SNP genotyping" (2005) Nature Genetics Supplement, 37:s5-s10.
Gunderson "A genome-wide scalable SNP genotyping assay using microarray technology" (2005) Nature Genetics, 37(5):s49-s54.
Steemers et al "Whole-genome genotyping with the single-base extension assay" (2006) Nature Methods, 3(1):31-33.
Garrick, BIF "Examples of Marker-Assisted Selection in Sheep and Cattle Improvement in New Zealand" (2003) Beef Improvement Federation 8th Genetic Prediction Workshop, 5-23.

van der Steen "Application of genomics to the pork industry" (2005) Journal of Animal Science, 83:E1-E8.
Meuwissen "Fine Mapping of a Quantitative Trait Locus for Twinning Rate Using Combined Linkage and Linkage Disequilibrium Mapping" (2002) Genetics, 161:373-379.
Lander and Green "Construction of multilocus genetic linkage maps in humans" (1987) Genetics, 84:2363-2367.
Cannings, Thompson, Skolnick "Probability Functions on Complex Pedigrees" (1978) Adv. Appl. Prob, 10(1):26-61.
Elston, Stewart "A General Model for the Genetic Analysis of Pedigree Data" (1971) Human Heredity, 21:523-542.
Haley and Visscher "Strategies to Utilize Marker-Quantitative Trait Loci Associations" (1998) Journal of Dairy Science, 81(2):85-97.
Georges and Massey "Velogenetics, or the Synergistic Use of Marker Assisted Selection and Germ-Line Manipulation" (1991) Theriogenology, 35(1):151-159.
Armstrong et al Gonadotropin Stimulation Regimens for Follicular Aspiration and in Vitro Embryo Production From Calf Oocytes (1994) Theruigenology, 42:1227-1236.
Syvanen "From Gels to Chips: "Minisequencing" Primer Extension for Analysis of Point Mutations and Single Nucleotide Polymorphisms" (1999) Human Mutation, 13:1-10.
McLean et al "Human Apolipoptein A mRNA" (1984) The Journal of Biological Chemistry, 259(10):6498-6504.
Lisanti et al "Characterization of Caveolin-rich Membrane Domains Isolated from an Endothelial-rich Source: Implications for Human Disease" (1994) The Journal of Cell Biology, 126:111-126.
Goddard and Hayes "Mapping genes for complex traitsin domestic animals and their use in breeding programmes" (2009) Nature Reviews, 10:381-391.
Habier et al "Genomic BLUP Decoded: A Look into the Black Box of Genomic Prediction" (2013) Genetics, 194:597-607.
International Search Report issued by the International Searching Authority (ISA/AU) dated Dec. 23, 2008 in connection with PCT International Patent Application No. PCT/AU2007/002006, 2 pages.
Supplemental European Search Report, dated Dec. 15, 2010 in connection with European Patent Application No. EP 07 85 5371, 3 pages.
Avendaño et al., (2003) Expected increases in genetic merit from using optimized contributions in two livestock populations of beef cattle and sheep. *Journal of Animal Science*, vol. 81 (12): pp. 2964-2975.
Beckmann et al., (2005) Haplotypes and haplotype-tagging single-nucleotide polymorphism: presentation Group 8 of genetic analysis workshop 14. *Genetic Epidemiology* (LISS, NY, US), vol. 29 (Supplemental 1): pp: S59-S71.
Boichard et al., (1997) The value of using probabilities of gene origin to measure genetic variability in a population. *Genetics Selection Evolution*, vol. 29 (3): pp. 5-23.
Cockett et al., (2001) Analysis of the sheep genome. *Physiol. Genomics* vol. 7: 69-78.
Cockett N. E., (1999) Genomics of Sheep. *AgBiotechNet*, vol. 1, ABN 013: pp. 1-3.
d'Andre Hirwa et al., (2010) Genes Related to Economically Important Traits in Beef Cattle. *Asian Journal of Animal Sciences* 5(1): 34-35, published online Jul. 27, 2010 at Scialert.net/abstract/?doi=ajas.2011.34.45.
Dekkers, (2004) Commercial application of marker- and gene-assisted selection in livestock: Strategies and lessons. *Journal of Animal Science*, vol. 82 (E Suppl.), E313-E328.
Gibbs et al., (2009) Genome-wide survey of SNP variation uncovers the genetic structure of cattle breeds. *Science*, vol. 324, p. 528.
Goddard & Hayes, (2007) Review Article: Genomic selection. *Journal of Animal Breeding and Genetics*, vol. 124, 323-330.
Halldórsson et al., (2004) Optimal Haplotype Block-Free Selection of Tagging SNPs for Genome-Wide Association Studies. *Genome Research*, vol. 14(8), 1633-1640.
Hayes & Goddard, (2003) Evaluation of marker assisted selection in pig enterprise. *Livestock Production Science*, vol. 81 (2-3) 2003: pp. 197-211.
Hayes & Goddard, (2001) The distribution of the effects of genes affecting quantitative traits in livestock. *Genetics Selection Evolution* (EPD Sciences, Les Ulis, FR), vol. 33 (3): pp. 209-229.

(56) References Cited

OTHER PUBLICATIONS

He et al., (2005) Linear reduction method for predictive and informative tag SNP selection. *International Journal of Bioinformatics Research and Applications*, vol. 1 (3): pp. 249-260.
Langdahl et al., (2000) Osteoporotic Fractures Are Associated with an 86-Base Pair Repeat Polymorphism in the Interleukin-1-Receptor Antagonist Gene But Not with Polymorphisms in the Interleukin-1β Gene. *Journal of Bone and Mineral Research*, vol. 15, p. 402.
Levenstien et al., (2006) Are Molecular Haplotypes Worth the Time and Expense? A Cost-Effective Method for Applying Molecular Haplotypes. *PLoS Genetics*, vol. 2(8), 1156-1166.
Lhuillier et al., (2006) Extensive Clonality and Strong Differentiation in the Insular Pacific Tree *Santalum insulare*: Implications for its Conservation. *Annals of Botany*, 98: 1061-1072.
Liu et al., (2005) Effective algorithms for tag SNP selection. *Journal of Bioinformatics and Computational Biology* (Imperial College Press, GB), vol. 3 (5): pp. 1089-1106.
Meuwissen et al., (2001) Prediction of Total Genetic Value Using Genome-Wide Dense Marker Maps. *Genetics*, vol. 157, 1819-1829.
Montaldo and Meza-Herrera, *Electronic Journal of Biotechnology* (Aug. 1998), vol. 1 (2): 83-89.
Mosig et al., (2001) A Whole Genome Scan for Quantitative Trait Loci Affecting Milk Protein Percentage in Israeli-Holstein Cattle, by Means of Selective Milk DNA Pooling in a Daughter Design, Using an Adjusted. False Discovery Rate Criterion. *Genetics*, vol. 157, p. 1683.
References cited in www.cattlenetwork.net/docs/library_rdb/molecular. htm, 42 pages, download date Apr. 7, 2013.
Ruane & Colleau, (1996) Marker-assisted selection for a sex-limited character in a nucleus breeding population. *Journal of Dairy Science* (American Dairy Science Association, US), vol. 79 (9): pp. 1666-1678.
Schaeffer, (2006) Strategy for applying genome-wide selection in dairy cattle. Journal of Animal Breeding and Genetics, vol. 123, 218-223.
Villanueva et al., (2005) Benefits from marker-assisted selection under an additive polygenic genetic model. *Journal of Animal Science*, vol. 83, 1747-1752.
Wall & Pritchard (2003) Haplotype blocks and linkage disequilibrium in the human genome. *Nature Reviews Genetics*, vol. 4, 587-597.
Walsh, (2001) Mintreview: Quantitative Genetics in the Age of Genomics. *Theoretical Population Biology*, vol. 59, 175-184.
Weller, (2007) Current and Future Developments in Patents for Quantitative Trait Loci in Dairy Cattle. *Recent Patents on DNA & Gene Sequences*, vol. 1: 69-76.
Woolliams et al., (1999) Expected Genetic Contributions and Their Impact on Gene Flow and Genetic Gain. *Genetics*, vol. 153, 1009-1020.
Zhao et al., (2003) Tests of candidate genes in breed cross population for QTL mapping in livestock. *Mammalian Genome*, vol. 14, p. 472.
Jun. 26, 2012 Office Action, issued in connection with U.S. Appl. No. 12/448,463.
Sep. 17, 2012 Response, filed in connection with U.S. Appl. No. 12/448,463.
Apr. 23, 2013 Office Action, issued in connection with U.S. Appl. No. 12/448,463.
Sep. 23, 2013 Response, filed in connection with U.S. Appl. No. 12/448,463.
Feb. 6, 2014 Office Communication, issued in connection with U.S. Appl. No. 12/448,463.
Written Opinion of the International Searching Authority (ISA/AU) issued in connection with PCT International Patent Application No. PCT/AU2007/002006, dated Dec. 23, 2008.
Hayes et al., (2006) Use of molecular markers to maximise diversity of founder populations for aquaculture breeding programs. Aquaculture, 255:573-578.

Statement of Grounds of Opposition filed on Jun. 19, 2014 in the Matter of Australian Patent Application No. 2007335195 in the name of Agriculture Victoria Services Pty Ltd and Opposition thereto by the Commonwealth Scientific and Industrial Research Organisation.
Statement and of Grounds and Particulars filed on Jun. 19, 2014 in the Matter of Australian Patent Application No. 2007335195 in the name of Agriculture Victoria Services Pty Ltd and Opposition thereto by Meat & Livestock Australia Limited.
First Declaration of Dorian J Garrick made Oct. 15, 2014 in the Matter of Australian Patent Application No. 2007335195 in the name of Agriculture Victoria Services Pty Ltd and Opposition thereto by the Commonwealth Scientific and Industrial Research Organisation.
Second Declaration of Dorian J Garrick made Nov. 18, 2014 in the Matter of Australian Patent Application No. 2007335195 in the name of Agriculture Victoria Services Pty Ltd and Opposition thereto by the Commonwealth Scientific and Industrial Research Organisation.
Third Declaration of Dorian J Garrick made Dec. 16, 2014 in the Matter of Australian Patent Application No. 2007335195 in the name of Agriculture Victoria Services Pty Ltd and Opposition thereto by the Commonwealth Scientific and Industrial Research Organisation.
First Declaration of Bruce Tier made Sep. 10, 2014 in the Matter of Australian Patent Application No. 2007335195 in the name of Agriculture Victoria Services Pty Ltd and Opposition thereto by Meat & Livestock Australia Limited.
Second Declaration of Bruce Tier made Sep. 17, 2014 in the Matter of Australian Patent Application No. 2007335195 in the name of Agriculture Victoria Services Pty Ltd and Opposition thereto by Meat & Livestock Australia Limited.
Declaration of Catherine Emily Winbanks made Sep. 12, 2014 in the Matter of Australian Patent Application No. 2007335195 in the name of Agriculture Victoria Services Pty Ltd and Opposition thereto by Meat & Livestock Australia Limited.
Declaration of James Hetzel made Mar. 19, 2015 in the Matter of Australian Patent Application No. 2007335195 in the name of Agriculture Victoria Services Pty Ltd and Opposition thereto by the Commonwealth Scientific and Industrial Research Organisation.
Declaration of James Hetzel made Dec. 23, 2014 in the Matter of Australian Patent Application No. 2007335195 in the name of Agriculture Victoria Services Pty Ltd and Opposition thereto by Meat & Livestock Australia Limited.
Declaration of Dorian J Garrick made May 22, 2015 in the Matter of Australian Patent Application No. 2007335195 in the name of Agriculture Victoria Services Pty Ltd and Opposition thereto by the Commonwealth Scientific and Industrial Research Organisation.
Declaration of Bruce Tier made Mar. 6, 2015 in the Matter of Australian Patent Application No. 2007335195 in the name of Agriculture Victoria Services Pty Ltd and Opposition thereto by Meat & Livestock Australia Limited.
Statement of Case dated Sep. 30, 2014 in the Matter of the New Zealand Patents Act 1953 and in the Matter of New Zealand Patent Application No. 577870 in the name of Agriculture Victoria Services Pty Limited and in the Matter of an Opposition thereto by Livestock Improvement Corporation under Section 21.
Counterstatement dated Dec. 19, 2014 in the Matter of the New Zealand Patents Act 1953 and in the Matter of New Zealand Patent Application No. 577870 in the name of Agriculture Victoria Services Pty Limited and in the Matter of an Opposition thereto by Livestock Improvement Corporation under Section 21.
Decision of the Commissioner in the Matter of the New Zealand Patents Act 1953 and in the Matter of New Zealand Patent Application No. 577870 in the name of Agriculture Victoria Services Pty Limited and in the Matter of an Opposition thereto by Livestock Improvement Corporation under Section 21, 13 pages.
Applicant's Submissions to the Australian Patent Office in the Matter of Australian Patent Application No. 2007335195 in the name of Agriculture Victoria Services Pty Ltd and Opposition thereto by the Commonwealth Scientific and Industrial Research Organisation and Meat & Livestock Australia Limited, 51 pages.

(56) References Cited

OTHER PUBLICATIONS

Commonwealth Scientific and Industrial Research Organisation's Submissions to the Australian Patent Office filed Feb. 10, 2016 in the Matter of Australian Patent Application No. 2007335195 in the name of Agriculture Victoria Services Pty Ltd and Opposition thereto by the Commonwealth Scientific and Industrial Research Organisation, 28 pages.
Meat & Livestock Australia Limited's Submissions to the Australian Patent Office filed Feb. 10, 2016 in the Matter of Australian Patent Application No. 2007335195 in the name of Agriculture Victoria Services Pty Ltd and Opposition thereto by Meat & Livestock Australia Limited.
Weller, J. I., Kashi, Y., & Soller, M. (1990). Power of daughter and granddaughter designs for determining linkage between marker loci and quantitative trait loci in dairy cattle. *Journal of dairy science*, 73(9), 2525-2537.
Windig, J. J., & Meuwissen, T. H. E. (2004). Rapid haplotype reconstruction in pedigrees with dense marker maps. *Journal of Animal Breeding and Genetics*, 121(1), 26-39.
Yamamoto, E., Matsunaga, H., Onogi, A., Ohyama, A., Miyatake, K., Yamaguchi, H., . . . & Fukuoka, H. (2017). Efficiency of genomic selection for breeding population design and phenotype prediction in tomato. *Heredity*, 118(2), 202-209.
Zhang, K., Qin, Z. S., Liu, J. S., Chen, T., Waterman, M. S., & Sun, F. (2004). Haplotype block partitioning and tag SNP selection using genotype data and their applications to association studies. *Genome Research*, 14(5), 908-916.
Third Party Observations filed Jun. 13, 2017 in connection with European Patent Application No. 07855371.6 (European Patent No. EP 2120543) including documents cited therein.
Baruch, E., Weller, J. I., Cohen-Zinder, M., Ron, M., & Seroussi, E. (2006). Efficient inference of haplotypes from genotypes on a large animal pedigree. *Genetics*, 172(3), 1757-1765.
Bernardo, R. (2001). What if we knew all the genes for a quantitative trait in hybrid crops?. *Crop Science*, 41(1), 1-4.
Blott, S., Kim, J. J., Moisio, S., Schmidt-Küntzel, A., Cornet, A., Berzi, P., . . . & Karim, L. (2003). Molecular dissection of a quantitative trait locus: a phenylalanine-to-tyrosine substitution in the transmembrane domain of the bovine growth hormone receptor is associated with a major effect on milk yield and composition. *Genetics*, 163(1), 253-266.
Calus, M. P. L. (2010). Genomic breeding value prediction: methods and procedures. *animal*, 4(2), 157-164.
Charlesworth, D., & Willis, J. H. (2009). The genetics of inbreeding depression. *Nature reviews. Genetics*, 10(11), 783.
Craig, D. W., & Stephan, D. A. (2005). Applications of whole-genome high-density SNP genotyping. *Expert review of molecular diagnostics*, 5(2), 159-170.
Gao, G., Hoeschele, I., Sorensen, P., & Du, F. (2004). Conditional probability methods for haplotyping in pedigrees. *Genetics*, 167(4), 2055-2065.
Garrick, D. J., Harris, B. L., & Johnson, D. L. (1997). The across-breed evaluation of dairy cattle in New Zealand. In *Proc. Assoc. Advmt. Anim. Breed Genet* (vol. 12, pp. 611-615).
Goddard, M. E. (1992). A mixed model for analyses of data on multiple genetic markers. *Theoretical and Applied Genetics*, 83(6-7), 878-886.
Grisart, B., Coppieters, W., Farnir, F., Karim, L., Ford, C., Berzi, P., . . . & Spelman, R. (2002). Positional candidate cloning of a QTL in dairy cattle: identification of a missense mutation in the bovine DGAT1 gene with major effect on milk yield and composition. *Genome research*, 12(2), 222-231.
Grisart, B., Farnir, F., Karim, L., Cambisano, N., Kim, J. J., Kvasz, A., . . . & Georges, M. (2004). Genetic and functional confirmation of the causality of the DGAT1 K232A quantitative trait nucleotide in affecting milk yield and composition. *Proceedings of the National Academy of Sciences of the United States of America*, 101(8), 2398-2403.
Multi-Breed Genetic Evaluation (2008), Beef Magazine. Retrieved from: http://www.beefmagazine.com/genetics/multibreed_genetic_evaluation#comment-0, 6 pages.

Kerr, R. J., & Kinghorn, B. P. (1996). An efficient algorithm for segregation analysis in large populations. *Journal of Animal breeding and Genetics*, 113(1-6), 457-469.
Lhuillier, E., Butaud, J. F., & Bouvet, J. M. (2006). Extensive clonality and strong differentiation in the insular Pacific tree *Santalum insulare*: implications for its conservation. *Annals of Botany*, 98(5), 1061-1072.
Mackinnon, M. J., & Georges, M. A. J. (1998). Marker-assisted preselection of young dairy sires prior to progeny-testing. *Livestock Production Science*, 54(3), 229-250.
Macrossan, P. E., Kinghorn, B. P., & Davis, G. P. (2001). Strategies for cost effective DNA testing for the Thryoglobulin gene in beef cattle. In *Association for the Advancement of Animal Breeding and Genetics* (vol. 14, pp. 309-312).
Sillanpää, M. J., & Arjas, E. (1998). Bayesian mapping of multiple quantitative trait loci from incomplete inbred line cross data. *Genetics*, 148(3), 1373-1388.
Sillanpää, M. J., & Arjas, E. (1999). Bayesian mapping of multiple quantitative trait loci from incomplete outbred offspring data. *Genetics*, 151(4), 1605-1619.
Marker-Assisted EPDs. The American Simmental Association's Fall Sire Summary, retrieved from http://www.simmental.org/site/index.php/genetic-evalution/genomics on Apr. 23, 2015, 1 page.
Smith, C., & Simpson, S. P. (1986). The use of genetic polymorphisms in livestock improvement. *Journal of Animal Breeding and Genetics*, 103(1-5), 205-217.
Soller, M. (1978). The use of loci associated with quantitative effects in dairy cattle improvement. *Animal Science*, 27(2), 133-139.
Stricker, C., Fernando, R. L., & Elston, R. C. (1995). Linkage analysis with an alternative formulation for the mixed model of inheritance: the finite polygenic mixed model. *Genetics*, 141(4), 1651-1656.
Syvänen, A. C. (2005). Toward genome-wide SNP genotyping. Nature genetics, 37, S5-S10.
Thallman, R. M., Moser, D. W., Dressler, E. W., Totir, L. R., Fernando, R. L., Kachman, S. D., . . . & Pollak, E. J. (Mar. 2005). Carcass merit project: DNA marker validation. In *Meeting Abstract*(pp. 5-15).
Thallman, R. M., Bennett, G. L., Keele, J. W., & Kappes, S. M. (2001). Efficient computation of genotype probabilities for loci with many alleles: I. Allelic peeling. *Journal of animal science*, 79(1), 26-33.
Thallman, R. M., Bennett, G. L., Keele, J. W., & Kappes, S. M. (2001). Efficient computation of genotype probabilities for loci with many alleles: II. Iterative method for large, complex pedigrees. *Journal of Animal Science*, 79(1), 34-44.
Tier, B. (2005). A Simple Generalisation of Kinghorn's Genotypic Probability Index. In *Proceedings of the Sixteenth Conference: Application of New Genetic Technologies to Animal Breeding*, Noosa Lakes, Queensland Australia, Sep. 25-28, 2005(vol. 45, No. 7-8). CSIRO Publishing.
Tier, B. (2006). Haplotyping for linkage disequilibrium mapping. In *Proceedings of the 8th World Congress on Genetics Applied to Livestock Production*, Belo Horizonte, Minas Gerais, Brazil, Aug. 13-18, 2006 (pp. 21-01). Instituto Prociência.
Van Eenennaam, A. (2005) A. DNA-Based Technologies. Chapter in Beef Sire Selection Manual, National Beef Cattle Evaluation Consortium (NBCEC).
Quaas, D., Thallman, M., Van Eenennaam, A. (2006). Presentation on Validating Genetic Markers.
Jul. 9, 2018 English Language Summary of Office Action dated May 29, 2018 in connection with Brazilian Patent Application No. 0721009-4.
Khatkar et al. (2004) "Quantitative trait loci mapping in dairy cattle: review and meta-analysis" Genet. Sel. Evol. 36:163-190.
Mar. 23, 2018 Third Party Observations cited in opposition against European Patent Application No. EP 07855371.6.
May 3, 2017 Allowed Specification in connection with European Patent Application No. EP 07855371.6.

\* cited by examiner

ARTIFICIAL SELECTION METHOD AND REAGENTS

RELATED APPLICATION DATA

This application is a continuation of U.S. Ser. No. 12/448,463, a § 371 national stage of PCT International Application No. PCT/AU2007/002006, filed Dec. 21, 2007, and claims the benefit of U.S. Provisional Application No. 60/876,623, filed Dec. 21, 2006, the contents of all of which are hereby incorporated herein by reference.

FIELD OF THE INVENTION

The present invention relates generally to the field of artificial selection, including the breeding of commercially-important animals and plants, and more specifically to methods and reagents for marker-assisted selection in animals and plants.

BACKGROUND OF THE INVENTION

Artificial selection programs are mainly concerned with increasing genetic gain by virtue of the contributions of more genes from "good" ancestors. The traditional means for determining genetic gain expresses gain as the product of selection intensity, accuracy, and genetic standard deviation defined in a single generation. Woolliams et al., *Genetics* 153, 1009-1020 (1999) showed that the process of contributing genes to a population involves more than a single generation and that sustained gain depends on Mendelian sampling variation entering the population in each generation. Put simply, genetic gain from artificial selection will be related to the genetic long-term contribution of an ancestor to the population as well as the marginal breeding value of an individual, thereby linking genetic gain to pedigree development.

For centuries, artificial selection has been entirely based on phenotype. Whilst this has proven useful, it is time-consuming and expensive. In particular, artificial selection based on phenotype may use progeny testing wherein the estimated breeding value of an individual is determined by performing multiple matings of the individual and determining the performance of the progeny for a particular trait or phenotypic character. For example, Schaeffer *J. Anim. Breed. Genet* 123, 218-223 (2006) estimated that the time taken to prove one Holstein bull takes approximately 64 months from conception to first proof, assuming a 9 month gestation period and that young bulls are test mated at one year of age and females are mated at 15 months of age. In this example, the total cost of proving one bull was estimated at about US $40,000, including the cost of housing and feeding the bull, collection and storage of semen, test matings and classification of daughters. However, the cost to an artificial insemination company that bulk purchases young bull calves for stud would be much greater, albeit offset by the return to service of any young bull.

Genomics has provided the prospect of artificial selection based on genotype. A complete genome sequence for a species enables the construction of any number of DNA chips or microarrays of about 10,000 or more nucleic acids each of which comprises a polymorphic marker. Knowledge of informative alleles, genes, polymorphisms, haplotypes or haplogroups etc for a particular QTL or trait facilitates the screening of individuals or germplasm and estimates of their EBV to be made. This is because genotypic selection relies upon the ability to genotype individuals for specific genes or markers that are either in linkage equilibrium (sparse markers) or linkage disequilibrium (dense markers) with a particular QTL or other locus of interest such that the breeding value of an individual can be estimated using marker haplotypes associated with the QTL or other locus. Genotypic selection is especially powerful where selection is desirably- or necessarily-independent of expression e.g., in the case of selection on milk production traits in male animals. Genotypic selection may not be pedigree-based, when the genotypic associations on which it is based are derived from a current population or, in the case of sparse marker maps, when the genotypic associations are derived from large half-sib family data or limited crosses.

Genotypic selection of "best" individuals can be based upon a score assigned to an informative allele, gene, polymorphism, haplotype or haplogroup etc of the individual alone, or in tandem with phenotype-based EBV or genotype-based EBV. Multiple bases for selection are preferred to minimize the loss in response to polygenes or other QTL. Walsh *Theor. Population Biol* 59, 175-184 (2001) also suggested that phenotype should remain a component in selection, to capture variation arising from new mutations and to prevent drastic reductions in effective population size, accumulated mutational variance from random genetic drift and the long term rate of response to selection that would otherwise arise from selection targeting specific genotypes.

Genotypic selection is facilitated by computational means, including resampling approaches e.g., randomisation tests and bootstrapping, which allow for the construction of confidence intervals and proper tests of significance e.g., Best Linear Unbiased Predictors (BLUP; Henderson In: "Applications of Linear Models in Animal Breeding", University of Guelph, Guelph, Ontario, Canada; Lynch and Walsh, In: "Genetics and Analysis of Quantitative Traits", Sunuaer Associates, Sunderland Mass., USA, 1998); the Markov Chain Monte Carlo (MCMC) approach (Geyer et al., *Stat. Sci.* 7, 73-511, 1992; Tierney et al., *Ann. Statist.* 21, 1701-1762, 1994; Tanner et al., In: "Tools for Statistical Analysis", Springer-Verlag, Berlin/New York, 1996); the Gibbs sampler (Geman et al., *IEEE Trans. Pattern Anal. Mach. Intell.* 6, 721-741, 1984); Bayesian posterior distribution (e.g., Smith et al., *J. Royal Statist. Soc. Ser.* B55, 3-23, 1993). Under Bayesian analysis, semi-subjective probabilities as to a population parameter are assigned to uncertainties and then analyzed and refined with experience, thereby permitting a prior belief about a population parameter to become updated to a posterior belief. For example, resampling-based Bayesian methods for multiple QTL mapping have been proposed by Sillanpaa and Arjas, *Genetics* 148, 1373-1388 (1998); Sillanpaa and Arjas, *Genetics* 151, 1605-1619 (1999); and Stephens and Fisch, *Biometrics* 54, 1334-1347 (1998). Meuwissen et al., *Genetics* 157, 1819-1829 (2001) simulated a genome of 1000 cM with markers assumed to be in linkage disequilibrium spaced 1 cM apart throughout the genome such that the markers were combined into haplotype pairs surrounding every 1 cM region, and compared least squares, BLUP and Bayesian approaches for estimating the effects of each haplotype pair simultaneously (50,00 haplotype effects in total) i.e., for the whole population and not specific to any one individual; the authors showed that the aggregate EBV could be determined for progeny provided that those animals were genotyped and the marker haplotypes were determined at an accuracy of 0.75-0.85 for all approaches. In this simulation, the effective population size was assumed to be constant.

Sparse marker maps can be constructed using markers in linkage equilibrium and spaced about 20 cM apart based upon large half-sib family data or limited crosses. For example, Georges et al, *Genetics* 139, 907-929 (1995) prepared a sparse genetic map of genetic markers that resulted in the detection of some QTL for milk production, and the inclusion of marker information into BLUP breeding values predicted a gain of 8-38% (Meuwissen and Goddard, *Genet. Sci. Evol.* 28, 161-176 (1996). However, the utility of such information is limited in outbreeding populations because the linkage phase between a marker and QTL must be established for each and every family in which the marker is to be used for selection. Accordingly, there are significant implementation problems with known sparse mapping approaches.

Dense marker maps, generally constructed from single nuclear polymorphisms (SNPs) and/or microsatellites provide for mapping of quantitative trait loci (QTL), association studies, and estimates of relatedness between individuals in a sample of a population. With dense marker maps, markers are more likely to be in linkage disequilibrium with a QTL and so more positively associated with a quantitative trait of interest than for a sparse map, such that selection does not require linkage phase to be established for each family. Markers in linkage disequilibrium are generally within about 1 cM to 5 cM of a locus of interest. Moreover, the identification of linkage disequilibrium markers requires candidate genes (Rothschild and Soller, *Probe* 8, p13, 1997) or fine mapping approaches (Anderson et al., *Nature Reviews Genet.* 2, 130-138, 2001). Thus, for a genome of about 3000 cM, about 3001 markers at 1 cM intervals or more are needed.

Notwithstanding the theoretical ability to produce dense genome-wide marker maps that theoretically cover whole genomes, there are several constraints on the application of such technology. Because there is an absolute requirement for the markers in such maps to be informative, the actual numbers of markers required are much larger than a theoretical minimum. Moreover, there is a need to construct haplotypes inherited from the parent(s) for each contiguous pair of bi-allelic markers, one of four possible informative haplotypes will be linked to a single QTL on average, and the frequencies of each haplotype will vary depending on the frequency of each contributing allele as well as the distance between the markers. This means that sufficient animals must be genotyped to ensure that all haplotypes are represented and their effects determined. The requirement for dense markers means that the number of animals required will also increase depending on genome size. Finally, dense marker maps do not exist for all species.

The high cost of genotyping renders it infeasible to implement all available markers across the genomes of most species. Such costs arise from the initial association of haplotype effects, which is correlated with the constraint referred to in the preceding paragraph, and the unit cost of genotyping an individual to estimate its breeding value. For example, in the case of cattle, Schaeffer *J. Anim. Breed. Genet* 123, 218-223 (2006) has estimated that a minimum of about 10,000 markers in a genome-wide dense marker map would be required, and that the approximate unit cost of genotyping one animal for this number of SNP markers is about US $400. The actual unit cost compares unfavourably with what would be acceptable to industry i.e., about US $20-200 per animal. However, if we assume that the haplotype effects are derived from 50 sire families with 50 sons each, the cost is closer to US $1,000,000. This cost will naturally increase if additional individuals are genotyped e.g., daughters of the sons in the proofs, in accordance with standard practice. Thus, to initialize a genome-wide scheme using dense marker maps is costly to implement, because of the large numbers of individuals that need to be genotyped to estimate haplotype effects and because of high unit costs. Such high costs hinder industry uptake of the technology. Methods for the cost-effective implementation of genome-wide selection using dense marker maps are not routinely available.

Several authors have proposed the identification of minimum informative subsets of SNPs that would permit reconstruction of haplotypes inferred by genotyping all other previously-known SNPs in a current population i.e., independent of pedigree, especially with reference to the human genome i.e., "tagging SNPs" (e.g., Avi-Itzhak et al., *Proc. Pacific Symposium Biocomputing* 8, 466-477, 2003; Hampe et al., *Hum. Genet.* 114, 36-43, 2003; Ke et al., *Bioinformatics* 19, 287-288, 2003; Meng et al., *Am. J. Hum. Genet.* 73, 115-130, 2003; Sebastiani et al., *Proc. Natl Acad. Sci USA* 100, 9900-9905, 2003; Stram et al., *Hum. Heredity* 55, 179-190, 2003 Thompson et al., *Hum. Heredity* 56, 48-55, 2003; Wang et al., *Hum. Mol, Genet.* 12, 3145-3149, 2003; Weale et al., *Am. J. Hum. Genet,* 73, 551-565, 2003; Halldórsson et al., *Genome Res,* 14, 1633-3640, 2006). Such methods require the determination of neighbourhoods of linkage disequilibrium in the genome to thereby determine those SNPs ("tagged SNPs") that can be used to infer each other (because they are linked). Such neighbourhoods may be haplotype blocks for which two SNPs are considered to be correlated if they occur in the same haplotype block with little evidence of recombination between them (e.g., Johnson et al., *Nature Genetics* 29, 233-237, 2001; Zhang et al., *Am. J. Hum. Genet.* 73, 63-73, 2003), or a union of possible haplotype blocks that contain particular SNPs (e.g., Halldórsson et al., *Genome Res.* 14, 1633-3640, 2006). Alternatively, neighbourhoods are deemed to consist of only those SNPs within a distance of less than 1 LD unit of each other based on metric LD maps (e.g., Maniatis et al., *Proc. Natl Acad. Sci USA* 99, 2228-2233, 2002). However, until recently there was no means of defining informativeness of tagged SNPs within the neighbourhoods of linkage disequilibrium i.e., determining how well any tagged SNP would characterize the genetic diversity or variance observed for the neighborhood, because the models used assumed that the genome regions dealt with were small and not many SNPs were involved. Zhang et al., *Am. J. Hum. Genet.* 73, 63-73 (2003) proposed a method for dealing with large data sets wherein chromosomes are partitioned into haplotype blocks and a set of tagging SNPs are selected within each block by imposing a cost for not tagging a given SNP in terms of the loss in haplotype diversity. Halldórsson et al., *Genome Res.* 14, 1633-3640 (2006) suggested an algorithmic framework for defining the informativeness of large SNP datasets in human chromosome 22, using a block-free method for determining neighbourhoods in linkage disequilibrium, which requires haplotype phase data to be available. Basically the informativeness measure of Halldórsson et al., is calculated by examining haplotype patterns for a set of neighbours of a target SNP, determining those pairs of haplotypes having different alleles at the target SNP, and then determining the proportion of those pairs of haplotypes that do not have the same set of alleles on all SNPs in the set of neighbours. Notwithstanding the advantages of tagging SNPs, such methods still require large numbers of SNPs to be genotyped.

Accordingly, there remains a need for informative and cost-effective methods of performing artificial selection using a genomics-based approach.

SUMMARY OF THE INVENTION

1. Definitions

The term "allele" refers to any one of the different forms of a gene or DNA sequence at a single locus i.e., chromosomal location including a coding sequence, non-coding sequence or regulatory sequence.

The term "amplified fragment length polymorphism" or "AFLP" refers to any one of different DNA fragment lengths produced by random-primed amplification of pooled or isolated restriction DNA fragments of genomic DNA or cDNA, wherein the fragment length varies between individuals in a population.

By "ancestor" is meant an individual having a genetic contribution to the current population. The term "ancestor" is thus a function of pedigree, the determination of which does not require prior knowledge of a particular trait or combination of traits present in the current population and its progenitors. Genotype information for an ancestor, as opposed to a founder, is generally incomplete as a consequence of poor record keeping and the absence of genetic material e.g., semen, from the ancestor to permit genotyping, such that missing genotypes of the ancestral population must be inferred to complete a genotype analysis. Ancestors in a pedigree may be overlapping, e.g., a sire and one of his sons, by virtue of contributing common genetic material to the current population notwithstanding any genes contributed independently by one or the other ancestor. To determine ancestry, the average relationship of a progenitor to the current population is determined excluding double-counting of overlapping ancestral contributions.

"Artificial selection" shall be taken to mean a selection under human control, including those systems, processes, steps or combinations of steps of a breeding program for producing genetic gain, including the collective design and/or implementation of said breeding program and intermediate steps by one or more persons. It is to be understood that artificial selection therefore requires a determination by man, based on a defined selection criterion or defined selection criteria, of one or more individuals in a population that are to be parents and ultimately ancestors, thereby producing a genetic gain as defined herein. This is distinct from the mere observation of population genetics e.g., for determining a genetic parameter such as heritability, diversity, inbreeding etc. Artificial selection systems include phenotypic selection and genotypic selection processes. Artificial selection steps include e.g., determining one or more of the following parameters: selection criteria and/or breeding objective(s); one or more selection indices; one or more selection targets; selection intensity; one or both sexual partners for a single mating or for multiple matings including references and/or replacements; the number of matings that any one or more individuals will contribute to a breeding program and the length of time that an individual will remain in a breeding population; generation interval; breeding value; or genetic gain. Artificial selection steps can also include e.g., performing one or more breeding steps based on a determination of one or more parameters supra and/or selecting progeny.

"Breeding objective" refers to a goal of an artificial selection program e.g., an improved germplasm. Breeding objective may be determined by weighted combination of traits defining an aggregate breeding value of an animal.

"Breeding value" means the genetic value of an individual as a parent in a breeding program and, more particularly, the effect of an individual's genes or genetic markers when considered in isolation or combination ("aggregate breeding value") on performance against a selection criterion or selection criteria.

Throughout this specification and the claims that follow, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

By "current population" is meant a population that are candidates for selection. Typically the current population includes individuals e.g., animals that are at or near an end-point in a pedigree.

As used herein the term "derived from" shall be taken to indicate that a specified integer may be obtained from a particular source albeit not necessarily directly from that source.

The term "effective population size" or "$N_e$" refers to the number of individuals in a population that contribute gametes to the next generation and preferably also to future generations. The effective population size is generally calculated as the number of breeding individuals in an idealized population that would show the same amount of dispersion of allele frequencies under random genetic drift or the same amount of inbreeding as a population under consideration. For example, in a randomly mating population consisting of 1000 individuals of which 500 are male are 500 are female with discrete generations, the expected fraction of the genes carried by any future generation contributed by any one animal in the current generation is 0.1% and the effective population size is the same as the absolute or real population size (N) i.e., 1000. However, because most populations are inbred to some degree, individuals do not select mates at random, generations may overlap, and fewer males generally breed than females, the effective population size typically has a value less than the absolute or real population size.

"Estimated breeding value" or "EBV" refers to a predicted breeding value of the progeny of a mating event, as determined by multiplying the ploidy of the organism in question by the progeny difference i.e., the difference between the average performances of an individual's progeny and the average performances of all progeny in a population assuming random mating. For a diploid organism, the progeny difference is doubled, because the breeding value is a measure of all genes for the organism, whereas the progeny difference is based upon the contribution of only one haploid genome from one parent. Progeny differences are based on average predicted performance of the progeny because each parent contributes the same number of genes to each progeny in the population.

By "founder" is meant an individual in a pedigree for which both parents are not known. Founders can be used in the method described herein in place of ancestors for when the known pedigree is incomplete and/or the genotypes of the ancestors are not known or able to be derived. The present invention has utility where genotypes of a founder population are used to infer the genotypes of the current population, however this is less preferred than using genotypes of the ancestors because it is expected that there are fewer key ancestors than founders. As the invention has a high level of accuracy when using genotypes of founders, the founder population can also serve as a suitable model for an ancestor population.

"Generation interval" means the amount of time required to replace one generation with the next and, in a closed population that is subject to artificial selection, the average age of parents when their selected progeny are born.

As used herein, the term "genetic gain" shall be taken to mean the average change in a heritable trait or combination of heritable traits from one generation to the next generation, including a predicted genetic gain and/or actual genetic gain More particularly, the average change is in the direction of one or more selection targets, or will at least avoid significant negative genetic gain i.e., an undesired effect for the selection criteria. The genetic gain can arise from artificial selection.

"Genotypic selection" means an artificial selection based upon the presence and/or absence of one or more genes or genetic markers of an individual associated with a particular gene, combination of genes, single-gene trait, quantitative trait, or combination of traits. Genotypic selection includes a diverse array of marker-assisted selection methods comprising the use of genetic markers e.g., alleles, haplotypes, haplogroups, loci, quantitative trait loci, or DNA polymorphisms [restriction fragment length polymorphisms (RFLPs), amplified fragment length polymorphisms (AFLPs), single nuclear polymorphisms (SNPs), indels, short tandem repeats (STRs). microsatellites and minisatellites] to, wherein the marker(s) is(are) determinative of the estimated breeding value of the individual.

A "haplogroup" is a cluster of similar haplotypes e.g., haplogroups of the human Y chromosome defined on the basis of unique mutation events in Y-STRs.

The term "haplotype" refers to a combination of alleles, loci or DNA polymorphisms that are linked so as to cosegregate in a significant proportion of gametes during meiosis. The alleles of a haplotype may be in linkage disequilibrium (LD).

The term "indel" refers to any one of different insertions or deletions of DNA at a particular allele or locus that are present in different individuals in a population. e.g., Y chromosome Alu polymorphisms (YAPs).

As used herein, the term "infer" or equivalent terms such as "inferring" or "inferred", e.g., the context of a genotype, haplotype, QTL, marker, etc., shall be taken to mean that a genotype is deduced from available information, and more particularly that missing information such as a missing genotype with respect to any one or more markers e.g., at a specific location in the genome of an individual is deduced. For example, a missing genotype for an ancestor (and/or founder) is "inferred" using genotype data of an individual in the current population related by pedigree to the ancestor (and/or founder), by performing the present invention as described according to one or more embodiments hereof. Alternatively, or in addition, a missing genotype for an individual of a current population is "inferred" using genotype data of an ancestor (and/or founder) related by pedigree to that individual, e.g., by employing one or more statistical means such as inter alia MCMV modelling. By such inferences, genotype data on both the ancestors (or founders) and the current population are made more complete than would otherwise be the case.

The term "linkage disequilibrium" or "LD" refers to alleles or loci or DNA polymorphisms that associate at a frequency higher than expected for independent alleles or markers, such that they appear as a haplotype. For example, when variants of two genetic loci are in strong linkage disequilibrium, the variant at one locus is predictive of the variant at the other locus on an individual chromosome.

In the present context, the term "mating" or similar term such as "mate" shall be construed without reference to kingdom or phylum to mean any sexual reproduction wherein a haploid genome is transferred from one individual of a population to another individual of a population, including the mating of one animal or cell (e.g., yeast cell) to another by natural or assisted means e.g., artificial insemination (AI); and the self-pollination of a plant or cross-pollination between plants.

"Mendelian sampling variation" means the variation in the deviation of the breeding value of an individual from the mean breeding values of its parents.

The term "minisatellite" refers to a variable number tandem repeat (VNTR) comprising more than about 5 repeats and from 6 to about 60 base pairs per repeat unit, wherein the number of repeat units varies between individuals in a population. As with microsatellites, changes may occur and the number of repeats may increase or decrease.

"Phenotypic selection" means an artificial selection based upon one, and possibly more, phenotypes of an individual. Phenotypic selection generally comprises progeny testing wherein the estimated breeding value of an individual is determined by performing multiple matings of the individual and determining the performance of the progeny.

In the present context, the term "population" means a group of individuals that potentially breed with each other such that they contribute genetically to the next generation, including but not limited to those individuals in a breeding program. The group can be of any size e.g., a species, breed, line, cultivar, herd or flock etc).

The term "quantitative trait" refers to a trait that is determined by expression of more than one gene.

The term "quantitative trait locus" or "QTL" refers to a region of DNA that is associated with a particular quantitative trait, wherein variation in the QTL is associated with variation in the quantitative trait as determined by genetic mapping or marker-assisted selection.

"Reference" means a parent or ancestor (and/or founder) that provides a genetic contribution to a number of groups of individuals, thereby permitting comparison of the performances of the progeny within and between groups relative to the performance of progeny from other parents or ancestors (and/or founders). References permit the best ancestors (and/or founders) to be selected and used in artificial selection.

"Replacement" means an individual that is to become a parent for the first time in an artificial selection program.

The term "restriction fragment length polymorphism" or "RFLP" refers to any one of different DNA fragment lengths produced by restriction digestion of genomic DNA or cDNA with one or more endonuclease enzymes, wherein the fragment length vanes between individuals in a population.

As used herein, the term "selection" shall be taken to refer to one or more systems, processes, steps or combinations of steps that determine one or more individuals in a population that are to contribute to the next generation, including natural selection and artificial selection.

"Selection criterion" refers to a phenotype or genotype forming the basis for a selection decision, including the presence or absence of one or more genes, or one or more genetic markers associated with a particular gene, combination of genes, trait or combination of traits.

"Selection index" means a ranking of a selection criterion or selection criteria according to a weighting or grade, used for estimating breeding value.

"Selection intensity" refers to the extent to which a breeder adhere to a decision on the selection of a particular individual or group of individuals for mating. Statistically, the selection intensity is determined as the difference between mean selection criterion of those individuals selected to contribute to the next generation and the mean selection criterion of all potential parents, expressed in standard deviation units.

"Selection target" refers to an optimum desired breeding value.

The term "short tandem repeat" or "STR" refers to a variable number tandem repeat (VNTR) comprising from 2 to about 5 or 6 base pairs per repeat unit, wherein the number of repeat units varies between individuals in a population. Microsatellites are an example of an STR that is generally highly polymorphic and randomly distributed in the genome and that may contain variability in sequence and/or for which the number of repeat units may increase or decrease.

The term "single-gene trait" refers to a trait that is determined by expression of one gene.

The term "single nucleotide polymorphism" or "SNP" refers to any one of different single nucleotides at a particular allele or locus varying between individuals in a population. Many SNPs are 2. Rationale Selection using marker data, e.g., derived from DNA markers, requires the genotypes of selection candidates to be known at those loci having an effect on traits within the breeding objective. This is likely to be a large number of markers and the list of such markers will expand as research provides additional linkage data.

In work leading to the present invention, the inventors reasoned that costs for selecting individuals from a population can be reduced if the selection candidates could be genotyped for a relatively small number of markers and preferably a constant set of markers. The inventors reasoned that such cost savings would be realized by genotyping the key ancestors of the selection candidates for useful markers, and preferably for all useful markers, and the selection candidates are genotyped for only a subset of those markers, and this is achievable by tracing chromosome segment(s) carrying the useful markers in a selection candidate to the corresponding chromosome segment(s) in a key ancestor from which the selection candidate has been derived. This would then make is possible for the markers genotyped on the chromosome segment of the key ancestor to be inferred for the corresponding chromosome segment of the selection candidate.

Although it is desirable that the key ancestors have been genotyped for all useful markers, this may not always be possible. For instance, no source of DNA from a key ancestor (and/or founder) may be available. In such circumstances, the inventors have reasoned that the genotype(s) of the key ancestor (and/or founder) for the markers may be inferred from that of suitable relatives that have been genotyped for those markers e.g., using an algorithmic approach that fills in missing values such as Markov Chain Monte Carlo (MCMV) modelling.

Although it is desirable for this purpose that the pedigree (s) of selection candidate(s) including relationships to one or more key ancestor(s) [and/or founder(s)] is(are) available, this may not always be possible. Often, such pedigrees either not available, because pedigree data are incomplete. In such circumstances, the inventors reasoned that the relationship (s) of the selection candidate(s) to the key ancestor(s) [and/or founder(s)] can be inferred using genetic markers that have been genotyped on both the selection candidates and the key ancestors. Alternatively, or in addition, founder animals within the known pedigree can be included in the analysis with the key ancestors.

The present invention is predicated on an understanding by the inventor that, for species having a small effective population size, the number of key ancestors (and often the number of founders) is small relative to the number of selection candidates. Therefore there is a saving in cost if the selection candidates are genotyped for only a subset of the markers whose genotyped are known or can be inferred on the key ancestors (and/or founders). It is possible to infer the missing genotypes of the selection candidates because the relationship between the selection candidates and the key ancestors (and/or founders) is known from the pedigree or inferred from other genetic markers. Methods of inferring missing genotypes that do not take advantage of the relationship between the selection candidates and the key ancestors (and/or founders) would be much less efficient and so the cost savings would be much less.

Moreover, the inventor has reasoned that basing informativeness of tagged markers on pedigree can derive additional cost-savings for genotyping individuals in a current population. More particularly, the inventor has reasoned that, for a species having a small effective population size, the diversity of the population is explained substantially by the sum those key ancestors (and/or founders) making a long term contribution to the population, and that diversity is inherited as neighbourhoods of chromosomal segments comprising ancestral markers, which may be in linkage disequilibrium (LD). Proceeding on this basis, the inventor has reasoned that the number of informative markers to be genotyped in an individual in a current population is reduced by inferring missing genotypes of a chromosome segment of an ancestor (and/or founder) contributing that chromosome segment to be the same as in the individual of the current population, and genotyping an informative marker within the chromosome segment. This differs from known tagging SNP methods which are independent of pedigree and generally require larger numbers of markers to be genotyped because they are based on haplotype blocks or a union of haplotype blocks, or require detailed metric LD maps.

3. Specific Embodiments

The present invention provides a method of artificial selection for a single gene or locus, including a single-gene locus or a QTL, said method comprising genotyping an individual in a current population for the presence or absence of one or more informative markers in a chromosome segment comprising a gene or locus of interest, inferring the genotype at the locus or QTL to be the same as in an ancestor (and/or founder) from which the chromosome segment is derived, and estimating the breeding value of the individual based on the inferred genotype, wherein the ancestor (and/or founder) is an ancestor (and/or founder) providing a significant long term genetic contribution to the current population and wherein the genotype of the ancestor (and/or founder) for the one or more informative markers and for the locus or QTL are known.

It will be understood that this method is more generally applicable to derive the genotype of an individual for any number of loci or QTL, in any number of chromosome locations. In accordance with this example, the present invention provides a method of artificial selection for one or more loci or QTL said method comprising genotyping an individual in a current population for the presence or absence of one or more informative markers in one or more chromosome segments each containing one or more loci or QTL of interest, inferring genotypes at the one or more loci or QTL to be the same as for an ancestor (and/or founder) from which a chromosome segment is derived, and estimating the breeding value of the individual based on the inferred genotypes, wherein one or more ancestors (and/or founders) is an ancestor (and/or founder) providing a significant long term genetic contribution to the current population, and wherein the genotypes of the one or more ancestors (and/or founders) for the one or more informative markers and for the loci or QTL are known.

In another example, the method can be used to derive the genotype of an individual, e.g., the genome-wide genotype. In accordance with this example, the present invention provides a method of artificial selection comprising genotyping an individual in a current population for the presence or absence of one or more informative markers in a plurality of chromosome segments, inferring genotypes of each chromosome segment to be the same in the individual as in one or more ancestors (and/or founders) from which the chromosome segments are derived, and estimating the breeding, value of the individual based on the inferred genotypes, wherein each ancestor (and/or founder) is an ancestor (and/or founder) providing a significant long term genetic contribution to the current population and wherein the genotypes of the one or more ancestors (and/or founders) for one or more informative markers is substantially known. Preferably, the genotype(s) of the one or more ancestors (and/or founders) for each informative marker is known, For deriving genome-wide genotype, it is preferred that the chromosome segments span the genome.

For genotyping applied to a single locus or QTL, multiple loci or QTLs, or genome-wide screening contexts, it is preferred that the genotyping of an individual comprises detecting one or more informative markers in a high-throughput system comprising a solid support consisting essentially of or having nucleic acids of different sequence bound directly or indirectly thereto, wherein each nucleic acid of different sequence comprises a polymorphic genetic marker derived from an ancestor (and/or founder) that is representative of the current population. Preferably, the high-throughput system comprises sufficient markers to be representative of the genome of the current population i.e., they span the entire genome and comprise sufficient polymorphic markers to be useful for genome-wide screening. The markers may be arrayed in linkage groups, optionally according to a chromosome segment with which they are in linkage disequilibrium. The marker information contained in the high throughput system can be obtained by an intermediate step in a method of the present invention.

As used herein, the term "genotyping an individual in a current population for the presence or absence of one or more informative markers" simply means to determine the presence or absence of the marker(s). The skilled artisan will be aware that whether a marker is selected for or against will depend upon the association of the marker for a desired genotype. The skilled artisan will also be aware that, in view of the aim of selecting breeding stock or germplasm for improving gain in future generations, the generality of the invention is not meant to be limited to determining the presence or absence of a specific genotype, haplotype or haplogroup, such as for a particular locus or QTL.

It is to be understood that the application of the present invention is not limited to any particular species, but determined by the effective population size of the species. Accordingly, the present invention is applicable to artificial selection in plants and animals having small effective population sizes. It is also to be understood that, because the selection of ancestors (and/or founders) is a function of pedigree, the present invention is also applicable to the selection of predominantly outbreeding and/or predominantly inbreeding species. Examples of populations to which the present invention is readily applied include cattle (e.g., beef and dairy cattle such as Holstein, Friesan, Holstein-Friesan, Braunvieh, Brown Swiss, Jersey, Danish Red, Aberdeen Angus), sheep (e.g., Meatlinc, Dorset x Rambouillet x. Finnsheep cross), pigs (e.g., Large White x Landrace cross, Large White, Duroc, Yorkshire, Landrace), poultry (e.g., Layers), fish (e.g., atlantic salmon), crustaceans, ryegrass, etc.

In accordance with the foregoing examples of the present invention, the current population will be a population of individuals having a small effective population size. This means that the effective population size should be less than the number of individuals in the current population required that would need to be genotyped to estimate all haplotype effects, and preferably less than one-half or less than one-third or less than one-quarter or about one-tenth of the numbers of individuals in the current population that would need to be genotyped to estimate haplotype effects. In terms of the actual numbers of ancestors (and/or founders) that would need to be genotyped in performing the present invention, this will vary depending on the population in question and the level of artificial selection that has been applied to the population in previous generations. For example, preferably this means less than about 1000 individuals, more preferably less than about 350 individuals, still more preferably less than about 250 individuals, still more preferably less than about 200 individuals and still more preferably less than about 150 or less than about 100 individuals. Alternatively, the effective population size is in the range of about 30-350 or about 30-200 or about 30-100 individuals. For populations larger than these estimates, the cost benefit of performing genomic selection based on ancestral lineage of chromosome segments is diminished.

An ancestor (and/or founder) providing a significant long term genetic contribution to the current population will preferably provide at least about 0.1% of the total variance to the current population and, more commonly at least about 0.5% or 1% of total variance. Particularly significant or "key" ancestors (and/or founders) generally provide at least about 2-10% of total variance to the current population e.g., 2% or 3% or 4% or 5% or 6% or 7% or 8% or 9% or 10%, however larger ancestral contributions are not to be excluded.

The markers may be any genetic marker e.g., e.g., one or more alleles, haplotypes, haplogroups, loci, quantitative trait loci, or DNA polymorphisms [restriction fragment length polymorphisms(RFLPs), amplified fragment length polymorphisms (AFLPs), single nuclear polymorphisms (SNPs), indels, short tandem repeats (STRs), microsatellites and minisatellites]. Conveniently, the markers are SNPs or STRs such as microsatellites, and more preferably SNPs. Preferably, the markers within each chromosome segment are in linkage disequilibrium.

The present invention clearly encompasses the performance of additional steps where informative data on the ancestors (and/or founders) is not known, including identifying and/or characterizing the ancestors (and/or founders) and/or establishing lineage of one or more chromosome segments. For example, the ancestors (and/or founders) can be characterized by obtaining and/or providing their genotypes e.g., for useful markers, a large number of useful markers or most markers using standard procedures for doing so, wherein said genotypes can also be inferred from data on their relatives e.g., using statistical means such as MCMV modelling to predict missing values. In one example, the ancestors (and/or founders) are characterized by providing and/or obtaining known genotypes and/or by inferring their genotypes.

Accordingly, in a further example, the inventive method comprises tracing the lineage of the one or more chromosome segment(s) back to one or more ancestors (and/or founders) from which they are derived. In accordance with this example, the present invention provides a method of artificial selection for a single gene or locus, including a single-gene locus or a QTL, said method comprising genotyping an individual in a current population for the presence or absence of one or more informative markers in a chromosome segment comprising a gene or locus of interest, tracing the lineage of the chromosome segment in the individual back to an ancestor (and/or founder) from which it is derived, inferring a genotype at the locus or QTL to be the same as in an ancestor (and/or founder) from which the chromosome segment is derived, and estimating the breeding value of the individual based on the inferred genotype, wherein the ancestor (and/or founder) is an ancestor (and/or founder) providing a significant long term genetic contribution to the current population and wherein the genotype of the ancestor (and/or founder) for the one or more informative markers and for the locus or QTL are known. For multiple loci or QTL at any number of chromosome locations, the invention provides a method of artificial selection for one or more loci or QTL said method comprising genotyping an individual in a current population for the presence or absence of one or more informative markers in one or more chromosome segments each containing one or more loci or QTL of interest, tracing the lineage of the one or more chromosome segments back to one or more ancestors (and/or founders) from which they are derived, inferring genotypes at the one or more loci or QTL to be the same as for an ancestor (and/or founder) from which a chromosome segment is derived, and estimating the breeding value of the individual based on the inferred genotypes, wherein one or more ancestors (and/or founders) is an ancestor (and/or founder) providing a significant long term genetic contribution to the current population, and wherein the genotypes of the one or more ancestors (and/or founders) for the one or more informative markers and for the loci or QTL are known. For genome-wide selection, the present invention provides a method of artificial selection comprising genotyping an individual in a current population for the presence or absence of one or more informative markers in a plurality of chromosome segments, tracing the lineages of the plurality of chromosome segments back to one or more ancestors (and/or founders) from which they are derived, inferring genotypes of each chromosome segment in the individual to be the same as in one or more ancestors (and/or founders) from which the chromosome segments are derived, and estimating the breeding value of the individual based on the inferred genotypes, wherein each ancestor (and/or founder) is an ancestor (and/or founder) providing a significant long term genetic contribution to the current population and wherein the genotypes of the one or more ancestors (and/or founders) for one or more informative markers is substantially known. Preferably, the genotype(s) of the one or more ancestors (and/or founders) for each informative marker is known. For deriving genome-wide genotype, it is preferred that the chromosome segments span the genome.

In yet another example, the inventive method comprises characterizing the ancestors (and/or founders) e.g., by genotyping one or more ancestors (and/or founders) for known markers. In accordance with this example, the present invention provides a method of artificial selection for a single gene or locus, including a single-gene locus or a QTL, said method comprising genotyping an individual in a current population for the presence or absence of one or more informative markers in a chromosome segment comprising a gene or locus of interest, tracing the lineage of the chromosome segment in the individual back to an ancestor (and/or founder) from which it is derived, genotyping the ancestor (and/or founder) for known markers, inferring a genotype at the locus or QTL to be the same as in an ancestor (and/or founder) from which the chromosome segment is derived, and estimating the breeding value of the individual based on the inferred genotype, wherein the ancestor (and/or founder) is an ancestor (and/or founder) providing a significant long term genetic contribution to the current population and wherein the genotype of the ancestor (and/or founder) for the locus or QTL is known. For multiple loci or QTL at any number of chromosome locations, the invention provides a method of artificial selection for one or more loci or QTL said method comprising genotyping an individual in a current population for the presence or absence of one or more informative markers in one or more chromosome segments each containing one or more loci or QTL of interest, tracing the lineage of the one or more chromosome segments back to one or more ancestors (and/or founders) from which they are derived, genotyping the one or more ancestors (and/or founders) for known markers, inferring genotypes at the one or more loci or QTL to be the same as for an ancestor (and/or founder) from which a chromosome segment is derived, and estimating the breeding value of the individual based on the inferred genotypes, wherein one or more ancestors (and/or founders) is an ancestor (and/or founder) providing a significant long term genetic contribution to the current population, and wherein the genotypes of the one or more ancestors (and/or founders) for the loci or QTL are known. For genome-wide selection, the present invention provides a method of artificial selection comprising genotyping an individual in a current population for the presence or absence of one or more informative markers in a plurality of chromosome segments, tracing the lineages of the plurality of chromosome segments back to one or more ancestors (and/or founders) from which they are derived, genotyping one or more ancestors (and/or founders) for known markers, inferring genotypes of each chromosome segment in the individual to be the same as in one or more ancestors (and/or founders) from which the chromosome segments are derived, and estimating the breeding value of the individual based on the inferred genotypes, wherein each ancestor (and/or founder) is an ancestor (and/or founder) providing a significant long term genetic contribution to the current population. For deriving genome-wide genotype, it is preferred that the chromosome segments span the genome.

In yet another example, the inventive method comprises identifying the ancestors (and/or founders) e.g., by determining a minimum set of ancestors (and/or founders) representative of the current population. In accordance with this example, the present invention provides a method of artificial selection for a single gene or locus, including a single-gene locus or a QTL, said method comprising genotyping an individual in a current population for the presence or absence of one or more informative markers in a chromosome segment comprising a gene or locus of interest, determining a minimum set of ancestors (and/or founders) representative of the current population, tracing the lineage of the chromosome segment in the individual back to an ancestor (and/or founder) from which it is derived, inferring a genotype at the locus or QTL to be the same as in an ancestor (and/or founder) from which the chromosome segment is derived, and estimating the breeding value of the individual based on the inferred genotype, wherein the genotype of the ancestor (and/or founder) for the one or more informative markers and for the locus or QTL is known. For multiple loci or QTL at any number of chromosome locations, the invention provides a method of artificial selection for one or more loci or QTL said method comprising genotyping an individual in a current population for the presence or absence of one or more informative markers in one or more chromosome segments each containing one or more loci or QTL of interest, determining a minimum set of ancestors (and/or founders) representative of the current population, tracing the lineage of the one or more chromosome segments back to one or more ancestors (and/or founders) from which they are derived, inferring genotypes at the one or more loci or QTL to be the same in an ancestor (and/or founder) from which a chromosome segment is derived, and estimating the breeding value of the individual based on the inferred genotypes, wherein the genotypes of the one or more ancestors (and/or founders) for the one or more informative markers and for the loci or QTL are known. For genome-wide selection, the present invention provides a method of artificial selection comprising genotyping an individual in a current population for the presence or absence of one or more informative markers in a plurality of chromosome segments, determining a minimum set of ancestors (and/or founders) representative of the current population, tracing the lineages of the plurality of chromosome segments back to one or more ancestors (and/or founders) from which they are derived, inferring genotypes of each chromosome segment in the individual to be the same as in one or more ancestors (and/or founders) from which the chromosome segments are derived, and estimating the breeding value of the individual based on the inferred genotypes, wherein the genotypes of the one or more ancestors (and/or founders) for the one or more informative markers are known. For deriving genome-wide genotype, it is preferred that the chromosome segments span the genome.

The present invention also encompasses situations where no information is known other than pedigree and perhaps limited information on the ancestor(s) and/or founder(s). In accordance with this example, the present invention provides a method of artificial selection for a single gene or locus, including a single-gene locus or a QTL, said method comprising genotyping an individual in a current population for the presence or absence of one or more informative markers in a chromosome segment comprising a gene or locus of interest, determining a minimum set of ancestors (and/or founders) representative of the current population, tracing the lineage of the chromosome segment in the individual back to an (and/or founder) from which it is derived, genotyping the (and/or founder) for known markers, inferring a genotype at the locus or QTL to be the same as in ancestor (or founder) from which the chromosome segment is derived, and estimating the breeding value of the individual based on the inferred genotype, wherein the genotype of the (and/or founder) for the locus or QTL is known. For multiple loci or QTL at any number of chromosome locations, the invention provides a method of artificial selection for one or more loci or QTL said method comprising genotyping an individual in a current population for the presence or absence of one or more informative markers in one or more chromosome segments each containing one or more loci or QTL of interest, determining a minimum set of ancestors (and/or founders) representative of the current population, tracing the lineage of the one or more chromosome segments back to one or more ancestors (and/or founders) from which they are derived, genotyping the one or more ancestors (and/or founders) for known markers, inferring genotypes at the one or more loci or QTL to be the same as in ancestor (or founder) from which a chromosome segment is derived, and estimating the breeding value of the individual based on the inferred genotypes, wherein the genotypes of the one or more ancestors (and/or founders) for the loci or QTL are known. For genome-wide selection, the present invention provides a method of artificial selection comprising genotyping an individual in a current population for the presence or absence of one or more informative markers in a plurality of chromosome segments, determining a minimum set of ancestors (and/or founders) representative of the current population, tracing the lineages of the plurality of chromosome segments back to one or more ancestors (and/or founders) from which they are derived, genotyping one or more ancestors (and/or founders) for known markers, inferring genotypes of each chromosome segment to be the same in the individual as in one or more ancestors (and/or founders) from which the chromosome segments are derived, and estimating the breeding value of the individual based on the inferred genotypes. For deriving genome-wide genotype, it is preferred that the chromosome segments span the genome.

In yet another example, individual chromosome segments in the selection candidates (ie members of the current population) are traced back to the key ancestors (and/or founders) by a process comprising tracing chromosome segments in selection candidates to one or more immediate ancestors (and/or founders) using a small number of markers and tracing the chromosome segments in the immediate ancestors (and/or founders) to corresponding chromosome segments in one or more key ancestors (and/or founders). Preferably, the chromosome segments in the immediate ancestors (and/or founders) are traced back to the chromosome segments in the key ancestors (and/or founders) using a larger number of markers. The tracing of chromosome segments to immediate ancestors (and/or founders) may minimise costs. For example, the immediate ancestors (and/or founders) may be all male animals used in the herd or flock in the last few generations. Since few males are used in most species, the number of immediate ancestors (and/or founders) is small compared to the number of selection candidates such that the cost of genotyping them for enough markers to trace chromosome segments back to key ancestors (and/or founders) is also reduced or minimized.

In yet another example, the pedigrees of the animals are not known but are inferred from the DNA markers that are used to trace chromosome segments. For example, the breed of animal may be unknown but deduced from the DNA markers.

In yet another example, the genome sequence of the key ancestors (and/or founders) is known and preferably complete, thereby permitting the near-complete or complete genome sequence of all current animals to be inferred, such as by tracing their chromosome segments back to key ancestors (and/or founders). Such genome sequence data are useful for selection.

In a particularly preferred example of genome-wide selection using SNPs, the present invention provides a method of artificial selection comprising:
(i) genotyping an individual in a current population for the presence or absence of one or more informative SNPs in a plurality of chromosome segments;
(ii) determining a minimum set of ancestors (and/or founders) representative of the current population;

(iii) tracing the lineages of the plurality of chromosome segments back to one or more ancestors (and/or founders) from which they are derived;
(iv) genotyping one or more ancestors (and/or founders) for known SNPs;
(v) inferring genotypes of each chromosome segment in the individual to be the same as in one or more ancestors (and/or founders) from which the chromosome segments are derived; and
(vi) estimating the breeding value of the individual based on the inferred genotypes.

For deriving genome-wide genotype, it is preferred that the chromosome segments span the genome.

It is to be understood that certain "steps" in the method of the invention can be performed in a different order to that described herein above, and at different points in time. For example, the method can be performed in the following order:
(i) optionally, determining a minimum set of ancestors (and/or founders) representative of the current population;
(ii) optionally, genotyping one or more ancestors (and/or founders) for known markers e.g., SNPs;
(iii) genotyping an individual in a current population for the presence or absence of one or more informative markers e.g., SNPs in one or a plurality of chromosome segments;
(iv) optionally, tracing the lineages of the one or plurality of chromosome segments back to one or more ancestors (and/or founders) from which they are derived;
(v) inferring genotypes of each chromosome segment in the individual of the current population to be the same as for one or more ancestors (and/or founders) from which the chromosome segments are derived; and
(vi) estimating the breeding value of the individual based on the inferred genotypes.

More particularly, the determination of ancestors (and/or founders) and/or genotyping of ancestors (and/or founders) can be separated from other "steps" in the method and/or performed beforehand e.g., to create a historical record for the individual, current population or species being selected. Alternatively or in addition, the tracing of lineages of chromosome segments is separated from other "steps" in the method, e.g., to create a similar historical record. The benefit of such historical records is that they can be utilized in future selections to further minimize expense. The present invention clearly encompasses such historical records in paper or electronic form and methods for their production and use.

Accordingly, the present invention also provides a computer-readable medium for use in artificial selection said computer-readable medium comprising a database of estimated breeding values for one or more individuals of a population having a small effective population size and optionally comprising data selected from the group consisting of: data on ancestors (and/or founders) for individuals; data on chromosome segments for individuals in the current population; data on chromosome segments for ancestors (and/or founders) of individuals in the current population; data on marker genotype(s) in chromosome segment(s) for individuals in the current population; data on marker genotype(s) in chromosome segment(s) for ancestors (and/or founders); data on lineages between the marker genotype(s) and/or chromosome segment(s); and combinations thereof. The estimated breeding values can be obtained by performing a method of the present invention.

The present invention also provides a computer system for use in artificial selection comprising:
(i) a database of estimated breeding values for one or more individuals of a population having a small effective population size and optionally comprising data selected from the group consisting of: data on ancestors (and/or founders) for individuals; data on chromosome segments for individuals in the current population; data on chromosome segments for ancestors (and/or founders) of individuals in the current population; data on marker genotype(s) in chromosome segment(s) for individuals in the current population; data on marker genotype(s) in chromosome segment(s) for ancestors (and/or founders); data on lineages between the marker genotype(s) and/or chromosome segment(s); and combinations thereof; and
(ii) a user interface allowing a user to input data pertaining to an individual e.g., chromosome segment, genetic marker, haplotype, haplogroup, nucleotide sequence or nucleotide occurrences for an individual e.g., for querying the database and displaying results of a database query.

Alternatively or in addition, the database consists essentially of the data on estimated breeding values of the one or more individuals any other data referred to herein above, or alternatively, consists exclusively of the data on estimated breeding values of the one or more individuals and any other data referred to herein above.

The present invention also provides a computer-readable medium for use in artificial selection said computer-readable medium comprising a database of marker genotype(s) of one or more ancestors (and/or founders) from one or more minimum sets of ancestors (and/or founders) each of which is representative of a population having a small effective population size wherein the marker genotypes are arrayed in linkage groups and optionally comprising data selected from the group consisting of: data on estimated breeding values for one or more individuals of a current population; data on ancestors (and/or founders) for individuals; data on chromosome segments for individuals in the current population; data on chromosome segments for ancestors (and/or founders) of individuals in the current population; data on marker genotype(s) in chromosome segment(s) for individuals in the current population; data on lineages between the marker genotype(s) and/or chromosome segment(s); and combinations thereof. The marker genotype(s) of one or more ancestors (and/or founders) arrayed in linkage groups can be obtained by performing a method of the present invention.

The present invention also provides a computer system for e in artificial selection comprising:
(i) a database of marker genotype(s) of one or more ancestors (and/or founders) from one or more minimum sets of ancestors (and/or founders) each of which is representative of a population having a small effective population size wherein the marker genotypes are arrayed in linkage groups and optionally comprising data selected from the group consisting of: data on estimated breeding values for one or more individuals of a current population; data on ancestors (and/or founders) for individuals; data on chromosome segments for individuals in the current population; data on chromosome segments for ancestors (and/or founders) of individuals in the current population; data on marker genotype(s) in chromosome segment(s) for individuals in the current population; data on lineages between the marker genotype(s) and/or chromosome segment(s); and combinations thereof; and
(ii) a user interface allowing a user to input data pertaining to an individual e.g., chromosome segment, genetic marker, haplotype, haplogroup, nucleotide sequence or nucleotide occurrences for an individual e.g., for querying the database and displaying results of a database query.

Alternatively or in addition, the database consists essentially of the marker genotype(s) of one or more ancestors (and/or founders) arrayed in linkage groups with or without any additional data referred to herein above, or consist exclusively of the marker genotype(s) of one or more ancestors (and/or founders) arrayed in linkage groups with or without any additional data referred to herein above.

In another example, the present invention also provides a computer-readable medium for use in artificial selection said computer-readable medium comprising a database of marker genotype(s) of one or more individuals of a population having a small effective population size and one or more minimum sets of ancestors (and/or founders) representative of the one or more individuals and the lineages between the marker of the one or more individuals and the ancestors (and/or founders), wherein the marker genotypes are arrayed in linkage groups. Optionally, the database also comprises data selected from the group consisting of: data on estimated breeding values for one or more individuals of a current population; data on ancestors (and/or founders) for individuals; data on chromosome segments for individuals in the current population; data on chromosome segments for ancestors (and/or founders) of individuals in the current population; and combinations thereof.

The present invention also provides a computer system for use in artificial selection comprising:
(i) a database of marker genotype(s) of one or more individuals of a population having a small effective population size and one or more minimum sets of ancestors (and/or founders) representative of the one or more individuals and the lineages between the marker of the one or more individuals and the ancestors (and/or founders), wherein the marker genotypes are arrayed in linkage groups, optionally also comprising data selected from the group consisting of: data on estimated breeding values for one or more individuals of a current population; data on ancestors (and/or founders) for individuals; data on chromosome segments for individuals in the current population; data on chromosome segments for ancestors (and/or founders) of individuals in the current population; and combinations thereof; and
(ii) a user interface allowing a user to input data pertaining to an individual e.g., chromosome segment, genetic marker, haplotype, haplogroup, nucleotide sequence or nucleotide occurrences for an individual e.g., for querying the database and displaying results of a database query.

Alternatively or in addition, the database consists essentially of the marker genotype(s) of the one or more individuals with or without any additional data referred to herein above, or consist exclusively of the marker genotype(s) of the one or more individuals with or without any additional data referred to herein above.

The present invention also provides a computer-readable medium for use in artificial selection said computer-readable medium comprising a database of chromosome segments present in the genomes of one or more individuals of a population having a small effective population size and one or more minimum sets of ancestors (and/or founders) representative of the one or more individuals, and the lineages between the chromosome segments of the one or more individuals and the ancestors (and/or founders). Optionally, the database also comprises data selected from the group consisting of: data on estimated breeding values for one or more individuals of a current population; data on ancestors (and/or founders) for individuals; data on marker genotype (s) in chromosome segment(s) for individuals in the current population; data on marker genotype(s) in chromosome segment(s) for ancestors (and/or founders); data on lineages between the marker genotype(s); and combinations thereof.

Preferably, data on the chromosome segments comprises marker genotype(s) in each chromosome segment and more preferably, data on the chromosome segments comprises marker genotype(s) in each chromosome segment and data on the lineages between the marker genotypes. The chromosome segments and any included marker genotype(s) of one or more ancestors (and/or founders) arrayed in linkage groups can be obtained by performing a method of the present invention.

The present invention also provides a computer system for use in artificial selection comprising:
(i) a database of chromosome segments present in the genomes of one or more individuals of a population having a small effective population size and one or more minimum sets of ancestors (and/or founders) representative of the one or more individuals, and the lineages between the chromosome segments of the one or more individuals and the ancestors (and/or founders), and optionally further comprising data selected from the group consisting of: data on estimated breeding values for one or more individuals of a current population; data on ancestors (and/or founders) for individuals; data on marker genotype(s) in chromosome segment(s) for individuals in the current population; data on marker genotype(s) in chromosome segment(s) for ancestors (and/or founders); data on lineages between the marker genotype (s); and combinations thereof; and
(ii) a user interface allowing a user to input data pertaining to an individual e.g., chromosome segment, genetic marker, haplotype, haplogroup, nucleotide sequence or nucleotide occurrences for an individual e.g., for querying the database and displaying results of a database query.

Alternatively or in addition, the database consists essentially of data on chromosome segments and any other data referred to herein above, or consist exclusively of data on chromosome segments and any other data referred to herein above.

The present invention also provides a high-throughput system for genotypic selection in a current population having a small effective population size, said system comprising a solid support consisting essentially of or having nucleic acids of different sequence bound directly or indirectly thereto, wherein each nucleic acid of different sequence comprises a polymorphic genetic marker derived from an (and/or founder) that is representative of the current population. Preferably, the high-throughput system comprises sufficient markers to be representative of the genome of the current population i.e., they span the entire genome and comprise sufficient polymorphisms to be useful for genome-wide screening. The markers may be arrayed in linkage groups, optionally according to the chromosome segment with which they are in linkage disequilibrium. It will be apparent from the foregoing description that the marker information contained in the high throughput system can be obtained by an intermediate step in a method of the present invention. In use, the high-throughput system of the present invention is used for genotyping at a single locus or QTL, or at multiple loci or QTLs, or for genome-wide genotyping of an individual in a current population.

It will also be understood that the artificial selection method of the present invention is useful for selecting an individual or reproductive or regenerative material from the individual for use in breeding, artificial insemination, in vitro fertilization, embryo implantation, or transgenic approach. Accordingly, the present invention also provides a process for producing genetic gain in a population comprising performing the method of the present invention according to any embodiment described herein and selecting an individual from a population having a high estimated breeding value. By "high estimated breeding value" means a breeding value sufficient to produce a genetic gain if the individual is mated to another individual in the population e.g., an individual that also has a high estimated breeding value as determined against the same or different parameter(s).

In one example, the process comprises obtaining reproductive or regenerative material from the selected individual. In the present context, the term "obtaining reproductive or regenerative material" shall be taken to include collecting and/or storing and/or maintaining germplasm such as the selected individual or semen, ova or pollen from the selected individual or embryos, seed etc produced using the germplasm of the selected individual, such as for use in conventional breeding programs or artificial insemination programs; and collecting and/or storing and/or maintaining cells such as embryonic stem cells, pluripotent or multipotent stem cells, fibroblasts, sperm cells, or organelles such as nuclei, mitochondria or chloroplasts from the selected individual, optionally transformed to include one or more genes or nucleic acids for conferring a desired attribute on an organism, for the production of transformed organisms carrying the genetic material of the selected individual.

The present invention clearly extends to any reproductive or regenerative material obtained by performing the process of the present invention. When reproductive or regenerative material used in this context deviates from one haploid genome of the selected individual, the present invention encompasses the use of that material to the extent that an organism produced therefrom produces a genetic gain in the population that is substantially the same as the expected genetic gain or actual genetic gain from the entire germplasm of the selected individual, This assumes a similar, isogenic or near-isogenic genetic background for the purposes of comparing genetic gain from a haploid genome of the selected individual to the expected or actual genetic gain from other contributing haploid genome proportions. As will be known to the skilled artisan, "expected genetic gain" is a theoretical value, whereas "actual genetic gain" is a value determined from test matings in a population.

The reproductive or regenerative material is generally stored for a prolonged period for subsequent use and it is desirable in such circumstances to maintain records of the material. Accordingly, the present invention also provides a computer-readable medium for use in artificial selection said computer-readable medium comprising a database of reproductive or regenerative material obtained by performing a process of the invention according to any embodiment described herein. Preferably, data on the reproductive or regenerative material is combined with data selected from the group consisting of: data on ancestors (and/or founders) for the material; data on chromosome segments for the material; data on chromosome segments for ancestors (and/or founders) of the material; data on marker genotype(s) in each chromosome segment for the material; data on marker genotype(s) in each chromosome segment for ancestors (and/or founders); data on lineages between the marker genotypes and/or chromosome segments; and combinations thereof.

The present invention also provides a computer system for use in artificial selection comprising:
(i) a database of reproductive or regenerative material obtained by performing a process of the invention according to any embodiment described herein, and optionally comprising data selected from the group consisting of: data on ancestors (and/or founders) for the material; data on chromosome segments for the material; data on chromosome segments for ancestors (and/or founders) of the material; data on marker genotype(s) in each chromosome segment for the material; data on marker genotype(s) in each chromosome segment for ancestors (and/or founders); data on lineages between the marker genotypes and/or chromosome segments; and combinations thereof; and
(ii) a user interface allowing a user to input data pertaining to an individual e.g., chromosome segment, genetic marker, haplotype, haplogroup, nucleotide sequence or nucleotide occurrences for an individual e.g., for querying the database and displaying results of a database query.

Alternatively or in addition, the database consists essentially of data pertaining to the reproductive or regenerative material obtained by performing a process of the invention according to any embodiment described herein, and optionally comprising data selected from the group consisting of: data on ancestors (and/or founders) for the material; data on chromosome segments for the material; data on chromosome segments for ancestors (and/or founders) of the material; data on marker genotype(s) in each chromosome segment for the material; data on marker genotype(s) in each chromosome segment for ancestors (and/or founders); data on lineages between the marker genotypes and/or chromosome segments; and combinations thereof. Alternatively, the database consists exclusively of such information.

In a further example, the present invention also provides a process for producing genetic gain in a population comprising:
(i) performing a method of the present invention according to any embodiment described herein for artificial selection;
(ii) selecting an individual from a population having a high estimated breeding value;
(iii) obtaining reproductive or regenerative material from the selected individual; and
(iv) producing one or more individuals or one or more generations of individuals from the reproductive or regenerative material.

The tem "producing one or more individuals or one or more generations of individuals from the reproductive or regenerative material" encompass traditional breeding approaches, artificial insemination, in vitro fertilization, embryo implantation, and transgenic approaches (e.g., using ES stem cells, pronuclei, sperm-mediated gene transfer, etc) known to the skilled artisan for the species to which the population belongs.

The present invention clearly extends to any individuals or generations of individuals produced by performing the process of the present invention. The skilled artisan will be aware that the genetic contribution of the reproductive or regenerative material may not be carried forward to all generations beyond an initial progeny generation. Accordingly, when generations of individuals beyond the initial progeny generation are produced from the reproductive or regenerative material, the present invention encompasses any individual of those generations to the extent that the individual contains in its genome a chromosome segment derived from the reproductive or regenerative material that would explain the expected genetic gain or actual genetic gain from the reproductive or regenerative material.

The present invention further provides a method for determining a set of ancestors (and/or founders) that is representative of a current population having a small effective population size, said method comprising determining the long term contributions of ancestors (and/or founders) to the population with reference to pedigrees of individuals of the current population and selecting those individuals providing the largest long term contributions to the current population such that the smallest number of ancestors (and/or founders) is selected to substantially describe the variance in the current population.

As used herein, the term "set of ancestors (and/or founders) that are representative of a current population" means that the set of ancestors (and/or founders) accounts for most of the variance in the current population i.e., the sum of all ancestors (and/or founders) in the set substantially describes the variance in the current population. By "substantially describe the variance in the current population" means at least about 70%, preferably at least about 80% and still more preferably at least about 90% of the total variance in the current population.

In another example, the present invention also provides a computer-readable medium for use in artificial selection said computer-readable medium comprising a database of one or more sets of ancestors (and/or founders) that are representative of one or more current populations having a small effective population size produced by performing a method described herein and optionally comprising additional data selected from the group consisting of: data on actual or estimated breeding values for one or more ancestors (and/or founders); data on chromosome segments for ancestors (and/or founders) of individuals in the current population; data on one or more markers contained within one or more chromosome segments for ancestors (and/or founders) of individuals in the current population; and combinations thereof.

The present invention also provides a computer system for use in artificial selection comprising:
(i) a database of one or more sets of ancestors (and/or founders) that are representative of one or more current populations having a small effective population size produced by performing a method described herein and optionally comprising additional data selected from the group consisting of: data on actual or estimated breeding values for one or more ancestors (and/or founders); data on chromosome segments for ancestors (and/or founders) of individuals in the current population; data on one or more markers contained within one or more chromosome segments for ancestors (and/or founders) of individuals in the current population and combinations thereof; and
(ii) a user interface allowing a user to input data pertaining to an individual e.g., chromosome segment, genetic marker, haplotype, haplogroup, nucleotide sequence or nucleotide occurrences for an individual e.g., for querying the database and displaying results of a database query.

The present invention clearly encompasses the use of any high throughput system, computer-readable medium or computer system referred to herein, or any combination thereof in artificial selection, artificial insemination, in vitro fertilization, embryo implant or transgenic procedure or process for producing genetic gain, and in any combination of such procedures or processes.

In each of the methods, processes, computer-readable media, computer systems and uses described herein, it is preferred that the pedigrees of individuals in the current population is complete or nearly complete i.e., comprising at least about 80% of ancestors (and/or founders), or 85% of ancestors (and/or founders) or 90% of ancestors (and/or founders) or 95% of ancestors (and/or founders) or 99% of ancestors (and/or founders) or 100% of ancestors (and/or founders). In such circumstances, the cumulative proportion of genes contributed by ancestors (and/or founders) to a current population will be at least about 80% and preferably at least about 90% or 95% or 99% or 100%. In cases where the pedigree data are incomplete, the present invention clearly encompasses the use of one or more markers to infer the pedigree of one or more animals of a current population that have an incomplete pedigree.

The foregoing embodiments describe the use of ancestor and/or founder genotypes to infer the genotypes of selection candidates in breeding programmes. However, it is to be understood that, notwithstanding the general applicability of the present invention to the use of ancestral and/or founder genotypes for this purpose, the use of ancestral genotypes is preferred because the data sets are generally smaller than for founder populations and therefore provide a greater advantage in terms of reduced costs than genotypes based on founder genotypes.

Each embodiment described herein is to be applied *mutatis mutandis* to each and every other embodiment unless specifically stated otherwise.

Throughout this specification and the claims that follow, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications as described herein or other than those specifically described, including functional equivalents. It is to be understood that the invention includes all such variations and modifications. The invention also includes all of the steps, features, compositions and compounds referred to or indicated in this specification, individually or collectively, and any and all combinations or any two or more of said steps or features.

The present invention is performed without undue experimentation using, unless otherwise indicated, conventional techniques of molecular biology, microbiology, virology, recombinant DNA technology, peptide synthesis in solution, solid phase peptide synthesis, and immunology.

The following texts are incorporated herein by reference:
1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp1-22; Atkinson et al., pp35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Perbal, B., A Practical Guide to Molecular Cloning (1984);
6. Bulmer, M. G., The mathematical theory of quantitative genetics. Clarendon Press, Oxford, (1980);
7. Falconer D. S., Introduction to Quantitative Genetics. Oliver & Boyd, London (1960);
8. Falconer D. S., Introduction to Quantitative Genetics, Second edition, Longmann, London (1981);
9. Falconer D. S., Introduction to Quantitative Genetics, Third edition, Longmann, London (1989);
10. Falconer D. S., Mackay T. F. C., Introduction to Quantitative Genetics. Fourth edition, Longmann & Co, London (1996); and 11. Kearsey M., Pooni H S., 1996. The Genetical Analysis of Quantitative traits. Chapman & Hall, London (1996).

DETAILED DESCRIPTION OF THE PREFERRED EMBODIMENTS

Species Having Small Effective Population Sizes (Ne)

The present invention is readily applied to any breeding or artificial selection context involving individuals from small effective populations, especially for populations which have had their effective population size reduced e.g., by selective breeding. Standard methods known to the skilled artisan are used to determine effective population size.

For example, the effective population size Ne is calculated as:

$$Ne = 1/(2\Delta F)$$

wherein F is the inbreeding coefficient, a measure of the amount of genetic diversity that has been lost such as by inbreeding. The term $\Delta F$ can be estimated by regressing individual inbreeding coefficients on generation number. The change in inbreeding per generation can then be used to estimate the effective number of breeding animals (Ne). The purpose of the effective population size is to estimate the number of animals that would produce an observed rate of inbreeding if bred under ideal conditions of random mating in the current generation (Lacy, Zoo Biol. 14, 565-578, 1995).

Examples of methods for determining effective population size are described in the referenced listed in Table 1. Preferred populations having a small effective population size will have been produced relatively recently e.g., over 4-10 generations, by virtue of a population bottleneck, or alternatively, over a period of time for which pedigree data on significant ancestors are available. This is to permit sufficient coverage of the genome of the current population to be inferred by haplotypes of the highly significant ancestors contributing the bulk of genetic variation to the current population. Examples of populations to which the present invention is readily applied include cattle (e.g., beef and dairy cattle such as Holstein, Friesan, Holstein-Friesan, Braunvieh, Brown Swiss, Jersey, Danish Red, Aberdeen Angus), sheep (e.g., Meatlinc, Dorset x Rambouillet x. Finnsheep cross), pigs (e.g., Large White x Landrace cross, Large White, Duroc, Yorkshire, Landrace), poultry (e.g., Layers), fish (e.g., atlantic salmon), crustaceans, ryegrass, etc. The estimated effective population size (Ne) of some of these animal populations are shown in Table 1 herein.

TABLE 1

| Species | Breed | Estimated Ne | Reference |
| --- | --- | --- | --- |
| Bovine | Holstein-Friesans | 50 | Boichard INRA Prod. Anim. 9, 323-335 (1996) |
| | Holstein-Friseans | 100 | Young et al., J. Dairy Sci. 79, 502-505 (1996) |
| | Braunvieh | 114 | Hagger, J. Anim. Breed. and Genet. 22, 405 (2005) |
| | Brown Swiss | 46 | Hagger, J. Anim. Breed. and Genet. 22, 405 (2005) |
| | Holstein | 49 | Sorensen et al., J Dairy Sci. 88, 1865-1872 (2005) |
| | Jersey | 53 | Sorensen et al., J Dairy Sci. 88, 1865-1872 (2005) |
| | Danish Red | 47 | Sorensen et al., J Dairy Sci. 88, 1865-1872 (2005) |
| Ovine | Dorset-Rarnboulliet-Finnsheep cross | 35 | Mackinnon et al., J. Anim Sci 81 (Supp. 1), p267 (2003) |
| Porcine | Large white—Landrace intercross | <200* | Harmegnies et al., Anim Genet. 37, 225-231 (2006) |
| | Large White | 200 | Nsengimana et al., Genetics 166, 1395-1404 (2004) |
| | Duroc/Large White | 85 | Nsengimana et al., Genetics 166, 1395-1404 (2004) |
| | Yorkshire/Large White | 60 | Nsengimana et al., Genetics 166, 1395-1404 (2004) |
| | Large White | 300 | Nsengimana et al., Genetics 166, 1395-1404 (2004) |
| | Landrace | 190 | Nsengimana et al., Genetics 166, 1395-1404 (2004) |
| Chickens | Layers | 91-123 | Hagger et al., J. Anim Breed Genet. 122 (Suppl 1), 15-21 (2005) |
| Atlantic Salmon | Breeding program population | 50-200 | Mork et al., Norges Offentlige Utredninger 9, 181-200 (1999) |

Defining Ancestors and Founders

Standard methods are used to determine ancestral/founder contributions to a current population, preferably in populations for which pedigree data are complete or near-complete e.g., at least about 80-90% complete or at least about 85-95% complete, and more preferably at least about 90% or 95% or 96% or 97% or 98% or 99% complete.

For example, the calculation derived by Boichard et al. (1997) can be used to identify the most influential ancestors and/or founders in a pedigree:

$$fa = \sum_{i=1}^{m} a_i^2$$

wherein ai is the marginal contribution of each ancestor/founder (i.e., any animal in the pedigree except for those animals in the current generation), as opposed to each founder, to the current generation, and m is the total number of contributing ancestors. The marginal contribution of all ancestors/founders should sum to one, and the effective number of ancestors is always smaller than or equal to the effective number of founders, individual contributions to the effective number of ancestors/founders can be used to find the most influential ancestors and/or founders. The numbers obtained from the calculation of fa take into consideration a decrease in genetic variation in populations that have passed through a bottleneck. It is the individual that passes on the most genes to a current population that makes the highest contribution. Even though an influential ancestor (e.g. a son of a sire) passes on most of his genes through many offspring, he only has half of the genes from his founding father. Animals in the current population under study are given a value of one and marginal contributions are obtained by processing the pedigree from youngest to oldest. When an important ancestor/founder is identified (an animal with the most relationships to the current population), their sire and dam information is removed from the pedigree, so contributions to the current population are not double-counted. An algorithm re-runs the calculations each time an ancestor is removed, so that marginal contributions not due to the ancestor already selected are the only ones measured (Boichard et al., *Genet. Sel. Evol.* 29, 5-23,1997).

From the example in the preceding paragraph, it is apparent that, if a son was selected as an important ancestor, his father would not get credit for his contributions through his influential son in the next iterate.

There is a discrepancy that may occur when fa is estimated through the previous equation. Since animals are selected based on their marginal contribution, if multiple animals have the same marginal contribution within one iteration, then the number of effective ancestors may change depending on which one is chosen. Large populations are not affected greatly, but in small populations there could be an increased effect on fa, since marginal contributions have the potential to be larger. The fa accounts for bottlenecks in the pedigree, but does not account for genetic drift. The calculation is useful for identifying the most influential ancestors, which may be of importance in selected populations.

Alternatively, significant ancestors and/or founders can be determined from considering the effect of different cohorts of ancestors/founders on genetic gain, as determined by studying the relationship between the long-term genetic contributions of ancestors/founders and index scores, essentially as described by Avendaño et al., *J. Anim. Sci.* 81, 2964-2975 (2003). In this method, the long-term contribution (r) is computed following the approach of Woolliams et al. *Anim. Sci.* 61, 177-187 (1995) wherein to compute r, a generation of ancestors/founders and a generation of descendants are defined according to average generation intervals previously calculated such that the ancestral and descendant generations are defined by using the generation interval (L). This definition ensures that r summed over all ancestors over a period of L yr equals unity (Bijma et al., *Genetics* 151, 1197-1210, 1990). Convergence of contributions is assumed if the variance of contributions of ancestors/founders across descendants is lower than $1.0 \times 10^{-4}$. The regression of the long-term genetic contribution of ancestors/founders on their index scores is calculated for each cohort of ancestors.

In a particularly preferred example, ancestors are defined by a method of the invention comprising determining the long term contributions of ancestors and/or founders to the population with reference to pedigrees of individuals of the current population and selecting those individuals providing the largest long term contributions to the current population such that the smallest number of ancestors and/or founders is selected to substantially describe the variance in the current population.

For example, let the following conditions or assumptions apply to the relationship of any ancestor or founder or group of ancestors or founders to a current population:
(i) n represents the number of potential ancestors and/or founders;
(ii) A is an n×n additive relationship matrix among n potential ancestors and/or founders;
(iii) c is an n×1 vector with the n potential ancestors and/or founders ordered in the same manner as in the additive relationship matrix A;
(iv) $c_i$ is the average relationship of ancestor/founder i to a current population i.e., the fraction of genes in the current population that are derived directly or indirectly from ancestor/founder i; and
(v) $A_m$ is a sub-matrix of A describing the relationship between in of the ancestors and/or founders;
(vi) $c_m$ is a sub-vector of c describing the relationship between m of the ancestors and/or founders and the current population;
(vii) p is a vector having element i equal to the proportion of genes in a population that derive only from ancestor/founder i; and
(viii) p'l is the proportion of genes in the population that derive from m ancestors and/or founders determined as a total of the elements of p.

Thus, $$p = A_m^{-1} c_m.$$

This means that the key ancestors and/or founders can be selected by determining a subset of ancestors that maximize p'l. For example, the most significant ancestors and/or founders to a population can be selected step-wise, by: (i) selecting an ancestor or founder contributing the highest proportion of genes to the current population; (ii) selecting an ancestor or founder that provides the highest marginal contribution of genes compared to the ancestor at (i); and (iii) conducting sufficient iterations of (ii) to substantially describe the variance in the current population.

For example, a set of about 25 significant ancestors in the Australian Holstein Fresian population has been determined using this approach, as shown in Table 2. The full names of these ancestors are also listed in Table 3 hereof providing a more complete listing of key ancestors and the availability of semen or genotype data on those key ancestors. One ancestor per line is indicated in both Table 2 and Table 3. In the example provided in Table 2, the cumulative proportion of genes contributed to current population is about 33%, possibly due to the incomplete pedigrees of animals in the current population. As can be seen from the data in Table 3, of 100 key ancestors, ony about one-half have been genotyped and there are limited semen stocks available for genotyping to be performed, thereby making inference of missing genotyes necessary.

It is preferable for the cumulative proportion of genes contributed to current population to be more than about 80% or 90% or 95% or 99% or 100%. In circumstances where this is not the case, it is preferred to use a population having better pedigree recording and/or to use markers themselves to infer the pedigree of animals with incomplete pedigrees.

TABLE 2

Exemplary key ancestors in the Australian Holstein Fresian cattle population

| Ancestor name | Cumulative Proportion of genes contributed to current population |
| --- | --- |
| VALIANT | 0.05371 |
| OAK RAG APPLE ELEVATION | 0.09220 |
| IVANHOE BELL | 0.12534 |
| STARBUCK | 0.15426 |
| MASCOT | 0.18180 |
| BLACKSTAR | 0.20459 |
| ENHANCER | 0.22700 |
| LINMACK KRISS KING | 0.24425 |
| ROTATE | 0.25660 |

TABLE 2-continued

Exemplary key ancestors in the Australian Holstein Fresian cattle population

| Ancestor name | Cumulative Proportion of genes contributed to current population |
| --- | --- |
| TRADITION CLEITUS | 0.26798 |
| ROYBROOK TELSTAR | 0.27699 |
| PACLAMAR ASTRONAUT | 0.28531 |
| FOND MATT | 0.29287 |
| WHITTIER-FARMS NED BOY | 0.29872 |
| ROYBROOK STARLITE | 0.30399 |
| WAPA ARLINDA CONDUCTOR | 0.30851 |
| ROSAFE CITATION | 0.31247 |
| CAM VIEW SOVEREIGN | 0.31638 |
| KIRK JUPITER | 0.32027 |
| TRAILYND ROYAL BEAU | 0.32374 |
| AGRO ACRES MARQUIS NED | 0.32717 |
| RONNYBROOK PRELUDE | 0.33046 |
| SUNNY BOY | 0.33379 |
| HILL NSPIRATION | 0.33658 |
| VIC KAI | 0.33915 |

TABLE 3

Exemplary key ancestors in the Australian and US Holstein Fresian cattle population

| AUS_ID | International_ID | Ancestor name | Semen stocks [1] | Genotype records [1] |
| --- | --- | --- | --- | --- |
| A00000013 | HOAUS000A00000013 | WARRAWEE ADEMA AMBASSADOR | 0 | 0 |
| A00000096 | HOAUS000A00000096 | KOTAHA KIM | 0 | 0 |
| A00000103 | HOAUS000A00000103 | VICTORIA OLSON | 0 | 0 |
| A00000193 | HOAUS000A00000193 | CAM VIEW SOVEREIGN | 0 | 0 |
| A00000207 | HOAUS000A00000207 | CLINELL RAELENE MAGIC | 0 | 0 |
| A00000253 | HOAUS000A00000253 | GLENJOY GRIFFLAND RANDY | 0 | 0 |
| A00001001 | HOAUS000A00001001 | SNIDERS FOND HOPE KING | 0 | 0 |
| A00001037 | HOAUS000A00001037 | FRASEA LORD JEWEL | 0 | 0 |
| A00001555 | HOAUS000A00001555 | HADSPEN BLITTERMAN 01 F B BUTTE | 0 | 0 |
| A00001643 | HOAUS000A00001643 | CLARIS VALE MASTER | 0 | 0 |
| A00001742 | HONZL000000062011 | PUKERORO ISAR IMPERIAL | 0 | 0 |
| A00001744 | HONZL000000044209 | GAYTON INGA VIC | 0 | 0 |
| A00001746 | HONZL000000005211 | WINDERMERE PERFECT MAX | 0 | 0 |
| A00001753 | HONZL000000007213 | LYNCREST S Q VICTOR | 0 | 0 |
| A00001756 | HONZL000000062147 | PUKERORO NORBERT LOCK | 0 | 0 |
| A00001786 | HONZL000000062387 | ATHOL SOVEREIGN FAME | 0 | 0 |
| A00001911 | HOGBR000000265781 | SUTTONHOO IDENA DIVIDEND PI | 0 | 0 |
| A00001931 | HOCAN000000292057 | FREELEA INKA JERRY | 0 | 0 |
| A00001938 | HOGBR000000303735 | MMB OAKRIDGES REFLECTION PI | 0 | 0 |
| A00001941 | HOCAN000000294213 | LINMACK KRISS KING | 0 | 0 |
| A00001957 | HOCAN000000313602 | AGRO ACRES REVENUE | 0 | 0 |
| A00001975 | HOGBR000000360323 | LOCUSLANE SUPREME | 0 | 0 |
| A00002138 | HOCAN000000280596 | EDGEWARE WAYNE ACHILLES | 0 | 0 |
| A00002142 | HOCAN000000289318 | TAYSIDE PABST ROCKMAN | 0 | 0 |
| A00002144 | HOCAN000000290516 | AGRO ACRES MARQUIS NED | 0 | 0 |
| A00002145 | HOCAN000000293299 | WAY BROOK SIR WINSTON | 0 | 0 |
| A00002148 | HOCAN000000302981 | MOOREVILLE ROCKET KEMP | 0 | 0 |
| A00002169 | HOCAN000000320891 | QUALITY ULTIMATE | 0 | 0 |
| A00002296 | HONZL000000062112 | PITCAIRNS T B TOPPER | 0 | 0 |
| A00002798 | HOCAN000000276333 | BOND HAVEN SOVEREIGN | 0 | 0 |
| A00002935 | HONZL000000000161 | KITEROA MUTUAL MIKE | 0 | 0 |
| A00002944 | HONZL000000027893 | OTAKI H C T GRAHAM | 0 | 0 |
| A00003116 | HOCAN000000364963 | ALBRECHT CASCADE | 0 | 0 |
| A00005113 | HOCAN000000299855 | FAIRLEA ROYAL MARK | 0 | 0 |
| A00005114 | HOCAN000000288790 | ROYBROOK TELSTAR | 0 | 0 |
| A00005147 | HOUSA000001392858 | NO-NA-ME FOND MATT | 0 | 0 |
| A00005158 | HOCAN000000267150 | ROSAFE CITATION R | 0 | 0 |
| A00005482 | HOUSA000001721509 | BROWNCROFT JETSON | 0 | 0 |
| A00006409 | HOUSA000001617348 | HILLIANA VALEDICTORIAN | 0 | 0 |
| A00006411 | HOUSA000001685359 | DONACRES DYNAMO-TWIN | 0 | 0 |
| A00006862 | HOUSA000001516360 | HEINDEL K C KIRK JUPITER | 0 | 0 |
| A00008144 | HONLD000311651443 | SKALSUMER SUNNY BOY | 0 | 0 |
| A00011920 | HONZL000000093290 | ATHOL MURRAYS EMINENCE | 0 | 0 |
| A00012752 | HONZL000000096329 | SRB COLLINS ROYAL HUGO | 0 | 0 |
| A00014530 | HOCAN000000259668 | GLENHOLM ALERT DEAN PABST | 0 | 0 |
| A00014543 | HODNK000000010763 | VAR ARLI | 0 | 0 |
| A00014643 | HOUSA000001282262 | ELLBANK ADMIRAL ORMSBY PRIDE | 0 | 0 |

TABLE 3-continued

Exemplary key ancestors in the Australian and US Holstein Fresian cattle population

| AUS_ID | International_ID | Ancestor name | Semen stocks [1] | Genotype records [1] |
|---|---|---|---|---|
| A00014647 | HOUSA000001242221 | POLYTECHNIC IMPERIAL KNIGHT | 0 | 0 |
| A00014648 | HOUSA000001199324 | SKOKIE BENEFACTOR | 0 | 0 |
| A00014679 | HOUSA000001531866 | PACLAMAR COMBINATION | 0 | 0 |
| A00014692 | HOUSA000001648394 | ACK-LEE CHIEF MONEY MAKER | 0 | 0 |
| A00017159 | HOUSA000001352979 | SKOKIE NED BOY | 0 | 0 |
| A00000378 | HOAUS000A00000378 | ONKAVALE GRIFFLAND MIDAS | 1 | 1 |
| A00001061 | HOAUS000A00001061 | TRAILYND ROYAL BEAU | 1 | 1 |
| A00001978 | HOGBR000000370161 | DALESEND CASCADE PI | 1 | 1 |
| A00002502 | HOCAN000000340909 | CAL-CLARK CUTLASS | 1 | 1 |
| A00004350 | HOCAN000000371440 | HANOVERHILL SABASTIAN ET | 1 | 1 |
| A00006720 | HOCAN000000402729 | MEADOW BRIDGE MANHATTAN | 1 | 1 |
| A00006889 | HOAUS000A00006889 | SHOREMAR PERFECT STAR (ET) | 1 | 1 |
| A00011268 | HONLD000829877874 | HOLIM BOUDEWIJN | 1 | 1 |
| A00006484 | HOUSA000001747862 | COR-VEL ENCHANTMENT | 1 | 2 |
| A00006968 | HOUSA000001772090 | CRESCENTMEAD CHIEF STEWART | 1 | 2 |
| A00014532 | HOCAN000000260599 | ROSAFE SHAMROCK PERSEUS | 1 | 2 |
| A00014669 | HOUSA000001563453 | WILLOW-FARM ROCKMAN IVANHOE | 1 | 2 |
| A00015051 | HOUSA000001483844 | HARBORCREST HAPPY CRUSADER | 1 | 2 |
| A00004325 | HOUSA000001781631 | ROBE-JAN SKYLER CHIEF | 1 | 1 |
| A00004805 | HOCAN000000363162 | HANOVER-HILL INSPIRATION | 1 | 1 |
| A00005146 | HOUSA000001626813 | MARSHFIELD ELEVATION TONY | 1 | 1 |
| A00005148 | HOUSA000001458744 | PACLAMAR ASTRONAUT | 1 | 1 |
| A00005149 | HOUSA000001450228 | PACLAMAR BOOTMAKER | 1 | 1 |
| A00005151 | HOUSA000001491007 | ROUND OAK RAG APPLE ELEVATION | 1 | 1 |
| A00005152 | HOUSA000001650414 | S-W-D VALIANT | 1 | 1 |
| A00005154 | HOUSA000001583197 | WAPA ARLINDA CONDUCTOR | 1 | 1 |
| A00005156 | HOUSA000001381027 | IDEAL FURY REFLECTOR | 1 | 1 |
| A00005424 | HOUSA000001806201 | WHITTIER-FARMS NED BOY | 1 | 1 |
| A00005425 | HOUSA000001667366 | CARLIN-M IVANHOE BELL | 1 | 1 |
| A00005426 | HOUSA000001682485 | SWEET-HAVEN TRADITION | 1 | 1 |
| A00005569 | HOUSA000001697572 | ARLINDA ROTATE | 1 | 1 |
| A00005707 | HOUSA000001879085 | BIS-MAY TRADITION CLEITUS | 1 | 1 |
| A00006187 | HOUSA000001929410 | TO-MAR BLACKSTAR-ET | 1 | 1 |
| A00006410 | HOUSA000001512026 | HARRISBURG GAY IDEAL | 1 | 1 |
| A00007236 | HOUSA000001930394 | HICKS-HOLLOW PROMPT | 1 | 1 |
| A00007435 | HOCAN000000392457 | A RONNYBROOK PRELUDE ET | 1 | 1 |
| A00007990 | HOUSA000001874634 | HOW-EL-ACRES K BELLMAN-ET | 1 | 1 |
| A00014631 | HOUSA000001399824 | HILLTOP APOLLO IVANHOE | 1 | 1 |
| A00014632 | HOUSA000001393997 | PROVIN MTN IVANHOE JEWEL | 1 | 1 |
| A00014636 | HOUSA000001428104 | SUNNYSIDE STANDOUT-TWIN | 1 | 1 |
| A00014670 | HOUSA000001560362 | C ROMANDALE SHALIMAR MAGNET | 1 | 1 |
| A00014702 | HOUSA000001608425 | ARLINDA CINNAMON | 1 | 1 |
| A00014705 | HOUSA000001674245 | I-O-STATE CHIEF FORD | 1 | 1 |
| A00002151 | HOCAN000000308691 | ROYBROOK STARLITE | 2 | 1 |
| A00002677 | HOCAN000000343514 | GLENAFTON ENHANCER | 2 | 1 |
| A00003460 | HOCAN000000352790 | HANOVERHILL STARBUCK | 2 | 1 |
| A00005339 | HOUSA000001856904 | THONYMA SECRET | 2 | 1 |
| A00006485 | HOUSA000001964484 | SOUTHWIND BELL OF BAR-LEE | 2 | 1 |
| A00006577 | HOCAN000000383622 | MADAWASKA AEROSTAR | 2 | 1 |
| A00007094 | HOUSA000002005253 | PICKARD-ACRES VIC KAI | 2 | 1 |
| A00007170 | HOUSA000002020049 | SINGING-BROOK N-B MASCOT-ET | 2 | 1 |
| A00008149 | HOUSA000002070579 | BIS-MAY S-E-L MOUNTAIN-ET | 2 | 1 |
| A00010003 | HONLD000775328514 | EASTLAND CASH | 2 | 1 |

[1], numbers indicate cumulative totals for Australia and US

Genotyping Methods

Genotyping generally involves detecting one or more markers of interest e.g., SNPs in a sample from an individual being tested, and analysing the results obtained to determine the haplotype of the subject. As will be apparent from the disclosure herein, it is particularly preferred to detect the one or more markers of interest using a high-throughput system comprising a solid support consisting essentially of or having nucleic acids of different sequence bound directly or indirectly thereto, wherein each nucleic acid of different sequence comprises a polymorphic genetic marker derived from an ancestor or founder that is representative of the current population and, more preferably wherein said high-throughput system comprises sufficient markers to be representative of the genome of the current population.

Suitable Samples for Genotyping

Preferred sample comprise nucleic acid, e.g., RNA or genomic DNA and preferably genomic DNA.

For example, genetic testing of plants can involve testing of any plant part e.g., leaf, floral organ, seed, etc.

Genetic testing of animals can be performed using a hair follicle, for example, isolated from the tail of an animal to be tested. Other examples of readily accessible samples include, for example, skin or a bodily fluid or an extract thereof or a fraction thereof. For example, a readily accessible bodily fluid includes, for example, whole blood, saliva, semen or urine. Exemplary whole blood fractions are selected from the group consisting of buffy-coat fraction, Fraction II+III obtainable by ethanol fractionation of Cohn (E. J. Cohn et al., J. Am. Chem. Soc., 68, 459 (1946), Fraction II obtainable by ethanol fractionation of Cohn (E. J. Cohn et al., *J. Am. Chem. Soc.*, 68, 459 (1946), albumin fraction, an immunoglobulin-containing fraction and mixtures thereof, Preferably, a sample from an animal has been isolated or derived previously from an animal subject by, for example, surgery, or using a syringe or swab.

In another embodiment, a sample can comprise a cell or cell extract or mixture thereof derived from a tissue or organ such as described herein above. Nucleic acid preparation derived from organs, tissues or cells are also particularly useful.

The sample can be prepared on a solid matrix for histological analyses, or alternatively, in a suitable solution such as, for example, an extraction buffer or suspension buffer, and the present invention clearly extends to the testing of biological solutions thus prepared. However, in a preferred embodiment, the high-throughput system of the present invention is employed using samples in solution.

Probe/Primer Design

The skilled artisan is aware that a suitable probe or primer i.e., one capable of specifically detecting a marker, will specifically hybridize to a region of the genome in genomic DNA from the individual being tested that comprises the marker. As used herein "selectively hybridizes" means that the polynucleotide used as a probe is used under conditions where a target polynucleotide is found to hybridize to the probe at a level significantly above background. The background hybridization may occur because of other polynucleotides present, for example, in genomic DNA being screened. In this event, background implies a level of signal generated by interaction between the probe and non-specific DNA which is less than 10 fold, preferably less than 100 fold as intense as the specific interaction observed with the target DNA. The intensity of interaction are measured, for example, by radiolabelling the probe, e.g. with $^{32}P$.

As will be known to the skilled artisan a probe or primer comprises nucleic acid and may consist of synthetic oligonucleotides up to about 100-300 nucleotides in length and more preferably of about 50-100 nucleotides in length and still more preferably at least about 8-100 or 8-50 nucleotides in length. For example, locked nucleic acid (LNA) or protein-nucleic acid (PNA) probes or molecular beacons for the detection of one or more SNPs are generally at least about 8 to 12 nucleotides in length. Longer nucleic acid fragments up to several kilobases in length can also be used, e.g., derived from genomic DNA that has been sheared or digested with one or more restriction endonucleases. Alternatively, probes/primers can comprise RNA.

Preferred probes or primers for use in the present invention will be compatible with the high-throughput system described herein. Exemplary probes and primers will comprise locked nucleic acid (LNA) or protein-nucleic acid (PNA) probes or molecular beacons, preferably bound to a solid phase. For example, LNA or PNA probes bound to a solid support are used, wherein the probes each comprise an SNP and sufficient probes are bound to the solid support to span the genome of the species to which an individual being tested belongs.

The number of probes or primers will vary depending upon the number of loci or QTLs being screened and, in the case of genome-wide screens, the size of the genome being screened. The determination of such parameters is readily determined by a skilled artisan without undue experimentation.

Specificity of probes or primers can also depend upon the format of hybridization or amplification reaction employed for genotyping.

The sequence(s) of any particular probe(s) or primer(s) used in the method of the present invention will depend upon the locus or QTL or combination thereof being screened. In this respect, the present invention can be generally applied to the genotyping of any locus or QTL or to the simultaneous or sequential genotyping of any number of QTLs or loci including genome-wide genotyping. This generality is not to be taken away or read down to a specific locus or QTL or combination thereof. The determination of probe/primer sequences is readily determined by a skilled artisan without undue experimentation.

Standard methods are employed for designing probes and/or primers e.g., as described by Dveksler (Eds) (In: PCR Primer: A Laboratory Manual, Cold Spring Harbour Laboratories, NY, 1995). Software packages are also publicly available for designing optimal probes and/or primers for a variety of assays, e.g., Primer 3 available from the Center for Genome Research, Cambridge, Mass., USA. Probes and/or primers are preferably assessed to determine those that do not form hairpins, self-prime, or form primer dimers (e.g. with another probe or primer used in a detection assay). Furthermore, a probe or primer (or the sequence thereof) is preferably assessed to determine the temperature at which it denatures from a target nucleic acid (i.e. the melting temperature of the probe or primer, or Tm). Methods of determining Tm are known in the art and described, for example, in Santa Lucia, *Proc. Natl. Acad. Sci. USA*, 95: 1460-1465, 1995 or Bresslauer et al., *Proc. Natl. Acad. Sci. USA*, 83: 3746-3750, 1986.

For LNA or PNA probes or molecular beacons, it is particularly preferred for the probe or molecular beacon to be at least about 8 to 12 nucleotides in length and more preferably, for the SNP to be positioned at approximately the centre of the probe, thereby facilitating selective hybridization and accurate detection.

For detecting one or more SNPs using an allele-specific PCR assay or a ligase chain reaction assay, the probe/primer is generally designed such that the 3' terminal nucleotide hybridizes to the site of the SNP. The 3' terminal nucleotide may be complementary to any of the nucleotides known to be present at the site of the SNP. When complementary nucleotides occur in both the probe/primer and at the site of the polymorphism, the 3' end of the probe or primer hybridizes completely to the marker of interest and facilitates, for example, PCR amplification or ligation to another nucleic acid. Accordingly, a probe or primer that completely hybridizes to the target nucleic acid produces a positive result in an assay.

For primer extension reactions, the probe/primer is generally designed such that it specifically hybridizes to a region adjacent to a specific nucleotide of interest, e.g., an SNP. While the specific hybridization of a probe or primer may be estimated by determining the degree of homology of the probe or primer to any nucleic acid using software, such as, for example, BLAST, the specificity of a probe or primer is generally determined empirically using methods known in the art.

Methods of producing/synthesizing probes and/or primers useful in the present invention are known in the art. For example, oligonucleotide synthesis is described, in Gait (Ed) (In: Oligonucleotide Synthesis: A Practical Approach, IRL Press, Oxford, 1984); LNA synthesis is described, for example, in Nielsen et al, *J. Chem. Soc. Perkin Trans.*, 1: 3423, 1997; Singh and Wengel, *Chem. Commun.* 1247, 1998; and PNA synthesis is described, for example, in Egholm et al., *Am. Chem. Soc.,* 114: 1895, 1992; Egholm et al., *Nature,* 365: 566, 1993; and Orum et al., *Nucl. Acids Res.,* 21: 5332, 1993.

Marker Detection Methods

Numerous methods are known in the art for determining the occurrence of a particular marker in a sample.

In a preferred embodiment, a marker is detected using a probe or primer that selectively hybridizes to said marker in a sample from an individual under moderate stringency, and preferably, high stringency conditions. If the probe or primer is detectably labelled with a suitable reporter molecule, e.g., a chemiluminescent label, fluorescent label, radiolabel, enzyme, hapten, or unique oligonucleotide sequence etc, then the hybridization may be detected directly by determining binding of reporter molecule. Alternatively, hybridized probe or primer may be detected by performing an amplification reaction such as polymerase chain reaction (PCR) or similar format, and detecting the amplified nucleic acid. Preferably, the probe or primer is bound to solid support e.g., in the high-throughput system of the present invention.

For the purposes of defining the level of stringency to be used in the hybridization, a low stringency is defined herein as hybridization and/or a wash step(s) carried out in 2-6× SSC buffer, 0.1% (w/v) SDS at 28° C., or equivalent conditions. A moderate stringency is defined herein as hybridization and/or a wash step(s) carried out in 0.2-2×SSC buffer, 0.1% (w/v) SDS at a temperature in the range 45° C. to 65° C., or equivalent conditions. A high stringency is defined herein as hybridization and/or a wash step(s) carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art.

Generally, the stringency is increased by reducing the concentration of SSC buffer, and/or increasing the concentration of SDS and/or increasing the temperature of the hybridization and/or wash. Those skilled in the art will be aware that the conditions for hybridization and/or wash may vary depending upon the nature of the hybridization matrix used to support the sample DNA, or the type of hybridization probe used.

Progressively higher stringency conditions can also be employed wherein the stringency is increased stepwise from lower to higher stringency conditions. Exemplary progressive stringency conditions are as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

For example, a change in the sequence of a region of the genome or an expression product thereof, such as, for example, an insertion, a deletion, a transversion, a transition, is detected using a method, such as, polymerase chain reaction (PCR), strand displacement amplification, ligase chain reaction, cycling probe technology or a DNA microarray chip amongst others.

Methods of PCR are known in the art and described, for example, in Dieffenbach (ed) and Dveksler (ed) (In: PCR Primer: A Laboratory Manual, Cold Spring Harbour Laboratories, NY, 1995). Generally, for PCR two non-complementary nucleic acid primer molecules comprising at least about 15 nucleotides, more preferably at least 20 nucleotides in length are hybridized to different strands of a nucleic acid template molecule, and specific nucleic acid molecule copies of the template are amplified enzymatically. PCR products may be detected using electrophoresis and detection with a detectable marker that binds nucleic acids. Alternatively, one or more of the oligonucleotides is/are labeled with a detectable marker (e.g. a fluorophore) and the amplification product detected using, for example, a lightcycler (Perkin Elmer, Wellesley, Mass., USA). Clearly, the present invention also encompasses quantitative forms of PCR, such as, for example, Taqman assays.

Strand displacement amplification (SDA) utilizes oligonucleotides, a DNA polymerase and a restriction endonuclease to amplify a target sequence. The oligonucleotides are hybridized to a target nucleic acid and the polymerase used to produce a copy of this region. The duplexes of copied nucleic acid and target nucleic acid are then nicked with an endonuclease that specifically recognizes a sequence at the beginning of the copied nucleic acid. The DNA polymerase recognizes the nicked DNA and produces another copy of the target region at the same time displacing the previously generated nucleic acid. The advantage of SDA is that it occurs in an isothermal format, thereby facilitating high-throughput automated analysis.

Ligase chain reaction (described, for example, in EP 320,308 and U.S. Pat. No. 4,883,750) uses at least two oligonucleotides that bind to a target nucleic acid in such a way that they are adjacent. A ligase enzyme is then used to link the oligonucleotides. Using thermocycling the ligated oligonucleotides then become a target for further oligonucleotides. The ligated fragments are then detected, for example, using electrophoresis, or MALDI-TOF. Alternatively, or in addition, one or more of the probes is labeled with a detectable marker, thereby facilitating rapid detection.

Cycling Probe Technology uses chimeric synthetic probe that comprises DNA-RNA-DNA that is capable of hybridizing to a target sequence. Upon hybridization to a target sequence the RNA-DNA duplex formed is a target for RNase H thereby cleaving the probe. The cleaved probe is then detected using, for example, electrophoresis or MALDI-TOF.

Additional methods for detecting SNPs are known in the art, and reviewed, for example, in Landegren et al, *Genome Research* 8: 769-776, 1998).

For example, an SNP that introduces or alters a sequence that is a recognition sequence for a restriction endonuclease is detected by digesting DNA with the endonuclease and detecting the fragment of interest using, for example, Southern blotting (described in Ausubel et al (In: Current Protocols in Molecular Biology. Wiley Interscience, ISBN 047 150338, 1987) and Sambrook et al (In: Molecular Cloning: Molecular Cloning: A Laboratory Manual, Cold Spring Harbor Laboratories, New York, Third Edition 2001)). Alternatively, a nucleic acid amplification method described supra, is used to amplify the region surrounding the SNP. The amplification product is then incubated with the endonuclease and any resulting fragments detected, for example, by electrophoresis, MALDI-TOF or PCR.

The direct analysis of the sequence of polymorphisms of the present invention can be accomplished using either the dideoxy chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)). For example, a region of genomic DNA comprising one or more markers is amplified using an amplification reaction, e.g., PCR, and following purification of the amplification product, the amplified nucleic acid is used in a sequencing reaction to determine the sequence of one or both alleles at the site of an SNP of interest.

Alternatively, one or more SNPs is/are detected using single stranded conformational polymorphism (SSCP). SSCP relies upon the formation of secondary structures in nucleic acids and the sequence dependent nature of these secondary structures. In one form of this analysis, an amplification method, such as, for example, a method described supra, is used to amplify a nucleic acid that comprises an SNP. The amplified nucleic acids are then denatured, cooled and analyzed using, for example, non-denaturing polyacrylamide gel electrophoresis, mass spectrometry, or liquid chromatography (e.g., HPLC or dHPLC). Regions that comprise different sequences form different secondary structures, and as a consequence migrate at different rates through, for example, a gel and/or a charged field. Clearly, a detectable marker may be incorporated into a probe/primer useful in SSCP analysis to facilitate rapid marker detection.

Alternatively, any nucleotide changes may be detected using, for example, mass spectrometry or capillary electrophoresis. For example, amplified products of a region of DNA comprising an SNP from a test sample are mixed with amplified products from an individual having a known genotype at the site of the SNP. The products are denatured and allowed to re-anneal. Those samples that comprise a different nucleotide at the position of the SNP will not completely anneal to a nucleic acid molecule from the control sample thereby changing the charge and/or conformation of the nucleic acid, when compared to a completely annealed nucleic acid. Such incorrect base pairing is detectable using, for example, mass spectrometry.

Allele-specific PCR (as described, for example, In Liu et al, *Genome Research*, 7: 389-398, 1997) is also useful for determining the presence of one or other allele of an SNP. An oligonucleotide is designed, in which the most 3' base of the oligonucleotide hybridizes to a specific form of an SNP of interest (i.e., allele). During a PCR reaction, the 3' end of the oligonucleotide does not hybridize to a target sequence that does not comprise the particular form of the SNP detected. Accordingly, little or no PCR product is produced, indicating that a base other than that present in the oligonucleotide is present at the site of SNP in the sample. PCR products are then detected using, for example, gel or capillary electrophoresis or mass spectrometry.

Primer extension methods (described, for example, in Dieffenbach (ed) and Dveksler (ed) (In: PCR Primer: A Laboratory Manual, Cold Spring Harbour Laboratories, N.Y., 1995)) are also useful for the detection of an SNP. An oligonucleotide is used that hybridizes to the region of a nucleic acid adjacent to the SNP. This oligonucleotide is used in a primer extension protocol with a polymerase and a free nucleotide diphosphate that corresponds to either or any of the possible bases that occur at the site of the SNP. Preferably, the nucleotide-diphosphate is labeled with a detectable marker (e.g. a fluorophore). Following primer extension, unbound labeled nucleotide diphosphates are removed, e.g. using size exclusion chromatography or electrophoresis, or hydrolyzed, using for example, alkaline phosphatase, and the incorporation of the labeled nucleotide into the oligonucleotide is detected, indicating the base that is present at the site of the SNP. Alternatively, or in addition, as exemplified herein primer extension products are detected using mass spectrometry (e.g., MALDI-TOF).

The present invention extends to high-throughput forms of primer extension analysis, such as, for example, minisequencing (Sy Vämen et al., *Genomics* 9: 341-342, 1995) wherein a probe or primer or multiple probes or primers is/are immobilized on a solid support (e.g. a glass slide), a sample comprising nucleic acid is brought into contact with the probe(s) or primer(s), a primer extension reaction is performed wherein each of the free nucleotide bases A, C, G, T is labeled with a different detectable marker and the presence or absence of one or more SNPs is determined by determining the detectable marker bound to each probe and/or primer.

Fluorescently labeled locked nucleic acid (LNA) molecules or fluorescently labeled protein-nucleic acid (PNA) molecules are useful for the detection of SNPs (as described in Simeonov and Nikiforov, *Nucleic Acids Research*, 30(17): 1-5, 2002). LNA and PNA molecules bind, with high affinity, to nucleic acid, in particular, DNA. Flurophores (in particular, rhodomine or hexachlorofluorescein) conjugated to the LNA or PNA probe fluoresce at a significantly greater level upon hybridization of the probe to target nucleic acid compared to a probe that has not hybridized to a target nucleic acid. However, the level of increase of fluorescence is not enhanced to the same level when even a single nucleotide mismatch occurs. Accordingly, the degree of fluorescence detected in a sample is indicative of the presence of a mismatch between the LNA or PNA probe and the target nucleic acid, such as, in the presence of an SNP. Preferably, fluorescently labeled LNA or PNA technology is used to detect a single base change in a nucleic acid that has been previously amplified using, for example, an amplification method described supra.

As will be apparent to the skilled artisan, LNA or PNA detection technology is amenable to a high-throughput detection of one or more markers immobilizing an LNA or PNA probe to a solid support, as described in Drum et al., *Clin. Chem*, 45: 1898-1905, 1999.

Similarly, Molecular Beacons are useful for detecting SNPs directly in a sample or in an amplified product (see, for example, Mhlang and Malmberg, *Methods* 25: 463-471, 2001). Molecular beacons are single stranded nucleic acid molecules with a stem-and-loop structure. The loop structure is complementary to the region surrounding the SNP of interest. The stem structure is formed by annealing two "arms" complementary to each other on either side of the probe (loop). A fluorescent moiety is bound to one arm and a quenching moiety that suppresses any detectable fluorescence when the molecular beacon is not bound to a target sequence bound to the other arm. Upon binding of the loop region to its target nucleic acid the arms are separated and fluorescence is detectable. However, even a single base mismatch significantly alters the level of fluorescence detected in a sample. Accordingly, the presence or absence of a particular base at the site of an SNP is determined by the level of fluorescence detected.

The present invention encompasses other methods of detecting an SNP that is, such as, for example, SNP microarrays (available from Affymetrix, or described, for example, in U.S. Pat. No. 6,468,743 or Hacia et al, Nature Genetics, 14: 441, 1996), Taqman assays (as described in Livak et al, *Nature Genetics*, 9: 341-342, 1995), solid phase minisequencing (as described in Syvämen et al. *Genomics*, 13: 1008-1017, 1992), minisequencing with FRET (as described in Chen and Kwok, *Nucleic Acids Res.* 25: 347-353, 1997)

or pyrominisequencing (as reviewed in Landegren et al., *Genome Res.*, 8(8): 769-776, 1998).

In those cases in which the polymorphism or marker occurs in a region of nucleic acid that encodes RNA, said polymorphism or marker is detected using a method such as, for example, RT-PCR, NASBA or TMA.

Methods of RT-PCR are known in the art and described, for example, in Dieffenbach (ed) and Dveksler (ed) (In: PCR Primer: A Laboratory Manual, Cold Spring Harbour Laboratories, NY, 1995).

Methods of TMA or self-sustained sequence replication (3SR) use two or more oligonucleotides that flank a target sequence, a RNA polymerase, RNase H and a reverse transcriptase. One oligonucleotide (that also comprises a RNA polymerase binding site) hybridizes to an RNA molecule that comprises the target sequence and the reverse transcriptase produces cDNA copy of this region. RNase H is used to digest the RNA in the RNA-DNA complex, and the second oligonucleotide used to produce a copy of the cDNA. The RNA polymerase is then used to produce a RNA copy of the cDNA, and the process repeated.

NASBA systems relies on the simultaneous activity of three enzymes (a reverse transcriptase, RNase H and RNA polymerase) to selectively amplify target mRNA sequences. The mRNA template is transcribed to cDNA by reverse transcription using an oligonucleotide that hybridizes to the target sequence and comprises a RNA polymerase binding site at its 5' end. The template RNA is digested with RNase H and double stranded DNA is synthesized. The RNA polymerase then produces multiple RNA copies of the cDNA and the process is repeated.

The hybridization to and/or amplification of a marker is detectable using, for example, electrophoresis and/or mass spectrometry. In this regard, one or more of the probes/primers and/or one or more of the nucleotides used in an amplification reactions may be labeled with a detectable marker to facilitate rapid detection of a marker, for example, a fluorescent label (e.g. Cy5 or Cy3) or a radioisotope (e.g. $^{32}$P).

Alternatively, amplification of a nucleic acid may be continuously monitored using a melting curve analysis method, such as that described in, for example, U.S. Pat. No. 6,174,670. Such methods are suited to determining the level of an alternative splice form in a biological sample.

Methods of the invention can identify nucleotide occurrences at SNPs using genome-wide sequencing or "microsequencing" methods. Whole-genome sequencing of individuals identifies all SNP genotypes in a single analysis. Microsequencing methods determine the identity of only a single nucleotide at a "predetermined" site. Such methods have particular utility in determining the presence and identity of polymorphisms in a target polynucleotide. Such microsequencing methods, as well as other methods for determining the nucleotide occurrence at SNP loci are discussed in Boyce-Jacino, et al., U.S. Pat. No. 6,294,336, incorporated herein by reference.

Microsequencing methods include the Genetic Bit Analysis method disclosed by Goelet, P. et al. (WO 92/15712, herein incorporated by reference). Additional, primer-guided, nucleotide incorporation procedures for assaying polymorphic sites in DNA have also been described (Komher et al, *Nucl. Acids. Res.* 17, 7779-7784, 1989; Sokolov, *Nucl. Acids Res.* 18, 3671 (1990); Syvanen et al., *Genomics* 8, 684-692, 1990; Kuppuswamy et al., *Proc. Natl. Acad. Sci.* (*U.S.A.*) 88, 1143-1147, 1991; Prezant et al, *Hum. Mutat.* 1, 159-164, 1992; Ugozzoli et al., *GATA* 9, 107-112, 1992; Nyren et al., *Anal. Biochem.* 208, 171-175, 1993; Wallace, WO89/10414; Mundy, U.S. Pat. No. 4,656,127; Cohen et al., French Pat. No. 2,650,840; WO91/02087). In response to the difficulties encountered in employing gel electrophoresis to analyze sequences, alternative methods for microsequencing have been developed, e.g., Macevicz, U.S. Pat. No. 5,002,867 incorporated herein by reference. Boyce-Jacino et al., U.S. Pat. No. 6,294,336 provide a solid phase sequencing method for determining the sequence of nucleic acid molecules (either DNA or RNA) by utilizing a primer that selectively binds a polynucleotide target at a site wherein the SNP is the most 3' nucleotide selectively bound to the target. Oliphant et al., *Suppl. Biotechniques*, June 2002, describe the use of BeadArray™ Technology to determine the nucleotide occurrence of an SNP, Alternatively, nucleotide occurrences for SNPs can be determined using a DNAMassARRAY system (Sequenom, San Diego, Calif.) is used, which sustem combines SpectroChips™, microfluidics, nanodispensing, biochemistry, and MALDI-TOF MS (matrix-assisted laser desorption ionization time of flight mass spectrometry).

Particularly useful methods include those that are readily adaptable to a high throughput format, to a multiplex format, or to both. High-throughput systems for analyzing markers, especially SNPs, can include, for example, a platform such as the UHT SNP-IT™ platform (Orchid Biosciences, Princeton, N.J., USA) MassArray™ system (Sequenom, San Diego, Calif., USA), the integrated SNP genotyping system (Illumina, San Diego, Calif., USA), TaqMan™ (ABI, Foster City, Calif., USA), Rolling circle amplification, fluorescent polarization, amongst others described herein above. In general, SNP-IT™ is a 3-step primer extension reaction. In the first step, a target polynucleotide is isolated from a sample by hybridization to a capture primer, which provides a first level of specificity. In a second step the capture primer is extended from a terminating nucleotide trisphosphate at the target SNP site, which provides a second level of specificity. In a third step, the extended nucleotide trisphosphate can be detected using a variety of known formats, including: direct fluorescence, indirect fluorescence, an indirect colorimetric assay, mass spectrometry, fluorescence polarization, etc. Reactions can be processed in 384 well format in an automated format using an SNPstream™ instrument (Orchid BioSciences, Princeton, N.J.).

High Throughput System for Genotypic Selection

The present invention also provides a high-throughput system for genotypic selection in a current population having a small effective population size, said system comprising a solid support consisting essentially of or having nucleic acids of different sequence bound directly or indirectly thereto, wherein each nucleic acid of different sequence comprises a polymorphic genetic marker derived from an ancestor or founder that is representative of the current population.

Exemplary high-throughput systems are hybridization mediums e.g., a microfluidic device or homogenous assay medium. Numerous microfluidic devices are known that include solid supports with microchannels (See e.g., U.S. Pat. Nos. 5,304,487, 5,110,745, 5,681,484, and 5,593,838). In a particularly preferred embodiment, the high throughput system comprises an SNP chip comprising 10,000-100,000 oligonucleotides each of which consists of a sequence comprising an SNP. Each of these hybridization mediums is suitable for determining the presence or absence of a marker associated with a trait.

The nucleic acids are typically oligonucleotides, attached directly or indirectly to the solid support. Accordingly, the oligonucleotides are used to determine the nucleotide occurrence of a marker associated with a trait, by virtue of the hybridization of nucleic acid from the subject being tested to an oligonucleotide of a series of oligonucleotides bound to the solid support being affected by the nucleotide occurrence of the marker in question e.g., by the presence or absence of an SNP in the subject's nucleic acid. Accordingly, oligonucleotides can be selected that bind at or near a genomic location of each marker. Such oligonucleotides can include forward and reverse oligonucleotides that can support amplification of a particular polymorphic marker present in template nucleic acid obtained from the subject being tested. Alternatively, or in addition, the oligonucleotides can include extension primer sequences that hybridize in proximity to a marker to thereby support extension to the marker for the purposes of identification. A suitable detection method will detect binding or tagging of the oligonucleotides e.g., in a genotyping method described herein.

Techniques for producing immobilised arrays of DNA molecules have been described in the art. Generally, most methods describe how to synthesise single-stranded nucleic acid molecule arrays, using for example masking techniques to build up various permutations of sequences at the various discrete positions on the solid substrate. U.S. Pat. No. 5,837,832, the contents of which are incorporated herein by reference, describes an improved method for producing DNA arrays immobilised to silicon substrates based on very large scale integration technology. In particular, U.S. Pat. No. 5,837,832 describes a strategy called "tiling" to synthesize specific sets of probes at spatially-defined locations on a substrate which are used to produce the immobilised DNA array. U.S. Pat. No. 5,837,832 also provides references for earlier techniques that may also be used.

DNA can be synthesised in situ on the surface of the substrate. However, DNA may also be printed directly onto the substrate using for example robotic devices equipped with either pins or piezo electric devices. Microarrays are generally produced step-wise, by the in situ synthesis of the target directly onto the support, or alternatively, by exogenous deposition of pre-prepared targets. Photolithography, mechanical microspotting, and ink jet technology are generally employed for producing microarrays.

In photolithography, a glass wafer, modified with photolabile protecting groups, is selectively activated e.g., for DNA synthesis, by shining light through a photomask. Repeated deprotection and coupling cycles enable the preparation of high-density oligonucleotide microarrays (see for example, U.S. Pat. No. 5,744,305, issued Apr. 28, 1998).

Microspotting encompasses deposition technologies that enable automated microarray production, by printing small quantities of pre-made target substances onto solid surfaces. Printing is accomplished by direct surface contact between the printing substrate and a delivery mechanism, such as a pin or a capillary. Robotic control systems and multiplexed print heads allow automated microarray fabrication.

Ink jet technologies utilize piezoelectric and other forms of propulsion to transfer biochemical substances from miniature nozzles to solid surfaces. Using piezoelectricity, the target sample is expelled by passing an electric current through a piezoelectric crystal which expands to expel the sample. Piezoelectric propulsion technologies include continuous and drop-on-demand devices. In addition to piezoelectric ink jets, heat may be used to form and propel drops of fluid using bubble-jet or thermal ink jet heads; however, such thermal ink jets are typically not suitable for the transfer of biological materials due to the heat which is often stressful on biological samples. Examples of the use of ink jet technology include U.S. Pat. No. 5,658,802 (issued Aug. 19, 1997).

A plurality of nucleic acids is typically immobilised onto or in discrete regions of a solid substrate. The substrate is porous to allow immobilisation within the substrate, or substantially non-porous to permit surface immobilization.

The solid substrate can be made of any material to which polypeptides can bind, either directly or indirectly. Examples of suitable solid substrates include flat glass, silicon wafers, mica, ceramics and organic polymers such as plastics, including polystyrene and polymethacrylate. It is also possible to use semi-permeable membranes such as nitrocellulose or nylon membranes, which are widely available. The semi-permeable membranes are mounted on a more robust solid surface such as glass. The surfaces may optionally be coated with a layer of metal, such as gold, platinum or other transition metal.

Preferably, the solid substrate is generally a material having a rigid or semi-rigid surface. In preferred embodiments, at least one surface of the substrate will be substantially flat, although in some embodiments it are desirable to physically separate synthesis regions for different polymers with, for example, raised regions or etched trenches. It is also preferred that the solid substrate is suitable for the high density application of DNA sequences in discrete areas of typically from 50 to 100 µm, giving a density of 10,000 to 40,000 cm-2.

The solid substrate is conveniently divided up into sections. This is achieved by techniques such as photoetching, or by the application of hydrophobic inks, for example teflon-based inks (Cel-line, USA).

Discrete positions, in which each different member of the array is located may have any convenient shape, e.g., circular, rectangular, elliptical, wedge-shaped, etc.

Attachment of the nucleic acids to the substrate can be covalent or non-covalent, generally via a layer of molecules to which the nucleic acids bind. For example, the nucleic acid probes/primers can be labelled with biotin and the substrate coated with avidin and/or streptavidin. A convenient feature of using biotinylated probes/primers is that the efficiency of coupling to the solid substrate is determined easily.

A chemical interface may be provided between the solid substrate e.g., in the case of glass, and the probes/primers. Examples of suitable chemical interfaces include hexaethylene glycol, polylysine. For example, polylysine can be chemically modified using standard procedures to introduce an affinity ligand.

Other methods for attaching the probes/primers to the surface of a solid substrate include the use of coupling agents known in the art, e.g., as described in WO98/49557.

The high-throughput system of the present invention is designed to determine nucleotide occurrences of one SNP or a series of SNPs. The systems can determine nucleotide occurrences of an entire genome-wide high-density SNP map.

High-throughput systems for analyzing markers, especially SNPs, can include, for example, a platform such as the UHT SNP-IT platform (Orchid Biosciences, Princeton, N.J., USA) MassArray™ system (Sequenom, San Diego, Calif., USA), the integrated SNP genotyping system (Illumina, San Diego, Calif., USA), TaqMan™ (ABI, Foster City, Calif., USA). Exemplary nucleic acid arrays are of the type described in WO 95/11995, WO 95/11995 also describes sub-arrays optimized for detection of a variant form of a pre-characterized polymorphism. Such a sub-array contains probes designed to be complementary to a second reference sequence, which is an allelic variant of the first reference sequence. The inclusion of a second group (or further groups) can be particularly useful for analyzing short sub-sequences of a primary reference sequence in which multiple mutations are expected to occur within a short distance commensurate with the length of the probes (e.g., two or more mutations within 9 to 21 bases). More preferably, the high throughput system comprises a SNP microarray such as those available from Affymetrix or described, for example, in U.S. Pat. No. 6,468,743 or Hacia et al, *Nature Genetics*, 14: 441, 1996.

DNA arrays are typically read at the same time by charged coupled device (CCD) camera or confocal imaging system. Alternatively, the DNA array can be placed for detection in a suitable apparatus that can move in an x-y direction, such as a plate reader. In this way, the change in characteristics for each discrete position are measured automatically by computer controlled movement of the array to place each discrete element in turn in line with the detection means.

The detection means is capable of interrogating each position in the library array optically or electrically. Examples of suitable detection means include CCD cameras or confocal imaging systems.

The system can further include a detection mechanism for detecting binding the series of oligonucleotides to the series of SNPs. Such detection mechanisms are known in the art.

The high-throughput system of the present invention can include a reagent handling mechanism that can be used to apply a reagent, typically a liquid, to the solid support.

The high-throughput system can also include a mechanism effective for moving a solid support and a detection mechanism.

Estimating Breeding Value

Any one of a number of statistical methods are used to estimate breeding value in the method of the present invention, preferably using computational means, including resampling approaches e.g., randomisation tests and bootstrapping, which allow for the construction of confidence intervals and proper tests of significance e.g., Best Liner Unbiased Predictors (BLUP; Henderson In: "Applications of Linear Models in Animal Breeding", University of Guelph, Guelph, Ontario, Canada; Lynch and Walsh, In: "Genetics and Analysis of Quantitative Traits", Sunuaer Associates, Sunderland Mass., USA, 1998); the Markov Chain Monte Carlo (MCMC) approach (Geyer et al., *Stat. Sci.* 7, 73-511, 1992; Tierney et al., *Ann. Statist.* 22, 1701-1762, 1994; Tanner et al., In: "Tools for Statistical Analysis", Springer-Verlag, Berlin/New York, 1996); the Gibbs sampler (Geman et al., *IEEE Trans. Pattern Anal. Mach. Intell.* 6, 721-741, 1984); Bayesian posterior distribution (e.g., Smith et al., *J. Royal Statist. Soc. Ser. B*55, 3-23, 1993). Such methods are well known to those skilled in the art.

Preferably, EBVs are calculated using a method designated "Bayes2" by Meuwissen et al., *Genetics* 157, 1819-1829 (2001). The Bayes 2 method allows some chromosome segments to have a larger effect on the trait than others. The statistical model could also fit the effect of each position on the genome using, for instance, BLUP to calculate the effect of any QTL alleles present at that position in all gametes represented in the population. Alternatively, the average relationship between the animals can be estimated from the marker alleles they have been inferred to carry, possibly weighting each position on the genome for its importance in controlling the trait. This assumes that each chromosome segment is derived from a key ancestor or founder within minimal or no recombination within the segment, an assumption that holds when the number of generations between the ancestor or founder and the individual of interest is low i.e., less than about 10 generations. For example, the matrix can be an identical-by-descent (IBD) matrix whose elements gij are the expectation of the number of chromosome segments carried by individual j that are IBD with a randomly sampled allele from individual i, conditional on pedigree information and the marker data. The IBD matrices can be computed for different chromosome segments e.g., spaced throughout the genome. The IBD matrices can also be averaged across positions and chromosomes. Different numbers of chromosome segments can be used to compute an IBD matrix. The accuracy of evaluation can be computed as the correlation between the true and the estimated breeding values.

For calculating EBV from genome-wide DNA markers, it is convenient to consider the process as comprising three steps:

1. Using the markers to deduce the genotype of each animal at each QTL;
2. Estimating the effect of each QTL genotype on the trait; and
3. Summing the QTL effects for selection candidates to obtain their genomic EBV (GEBV).

These steps are described in more detail in the following paragraphs.

Using the Markers to Deduce the Genotype of Each Animal at Each QTL

The simplest method to deduce QTL genotypes is to treat the markers as if they were QTL and to estimate the effects of the markers alleles or genotypes. The key parameter here is the proportion of the QTL variance explained by the markers ($r^2$). This is dependent on the LD between the QTL and one marker or a linear combination of markers, The extent of LD and hence $r^2$ are highly variable. Average $r^2$ declines as the distance between the two loci increases. For example, in Holstein cattle the average $r^2$ when loci are 50 kb apart is 0.35. To obtain an average spacing of 50 kb requires 60,000 evenly spaced markers. As the markers are unlikely to be evenly spaced, and due to the variable nature of LD, we could still not expect that all QTLs would have a SNP in complete LD with them. This suggests we need denser markers than are currently available. The technology to achieve this is available (eg. Parks et al, *Nature Genet.* on line publication Jun. 6, 2007).

An alternative to using single marker genotypes is to construct haplotypes based on several markers. A QTL that is not in complete LD with any individual marker may be in complete LD with a multi-marker haplotype. For example, using 9323 SNP genotypes from Angus cattle, and considering a randomly chosen SNP as a surrogate for a QTL, the proportion of variance explained by a haplotype of surrounding markers can increase from 0.2 for the nearest marker to 0.58 for a 6-marker haplotype, The use of multiple marker genotypes but without deducing haplotypes, for example with multiple marker regression, will generally be between these two limits. Typically there are many haplotypes present in a population and so the amount of data with which to estimate the effect of each one is reduced and this will reduce the accuracy with which each haplotype effect is estimated. However, the increase in QTL variance explained from using marker haplotypes more than compensates for the decrease in accuracy of estimating a greater number of haplotype effects, so that haplotypes predict the effect of the QTL alleles more accurately than a single marker. The advantage of haplotypes over single markers decreases as the $r^2$ between adjacent markers increases. At $r^2$=0.215 between adjacent markers, the haplotype approach and single marker approach provide very similar accuracies.

As the total number of animals with phenotypes and marker genotypes increases, the accuracy of estimating marker genotype effects will approach 1.0 and so will the accuracy of estimating haplotype effects. But the accuracy for haplotype will approach 1.0 more slowly than the accuracy of estimating SNP effects because there are more than 2 haplotypes effects per QTL to be estimated. Therefore the advantage of haplotypes over single markers increases as the amount of data for estimation increases, especially at lower marker densities. The accuracy of using single markers can be greater than using marker haplotypes if there is a limited number of phenotypic records to estimate the effects and the level of LD between the single markers and QTLs is very high.

An alternative to treating a haplotype of markers as if it were a QTL allele is to treat every gamete as carrying a different QTL allele but to estimate the correlation among the effects of these alleles based on the surrounding markers. A linkage analysis traces the QTL alleles through the known pedigree using the markers and calculates the probability that any two alleles are identical by descent (IBD) from a common ancestor or founder within the pedigree. The probability that two QTL alleles are IBD due to a common ancestor or founder outside the pedigree can be assessed from the similarity of the marker alleles surrounding the QTL by assuming an evolutionary model for the linkage disequilibrium between the markers and the QTLs. The linkage analysis and the LD analysis can be combined to estimate a matrix of IBD probabilities between all QTL alleles and this can be used to estimate the effects of all QTL alleles. Errors in the positioning of markers on the genome will reduce the accuracy of inferring haplotypes, and the therefore the accuracy of GEBVs resulting from both the haplotype and IBD approaches.

At low marker densities (eg. $r^2$ between adjacent markers less than 0.2) the IBD approach is preferred over the haplotype approach or single marker approach. At high marker densities, the three methods provide approximately the same accuracy.

Estimating the Effect of Each QTL Genotype on the Trait

Genetic gain is greatest if the estimate of breeding value (g) has the property GEBV=E(g|"data"). Since the EBV is calculated by summing the estimated effects of all QTLs (u), the desired property for the EBV is achieved by estimating each QTL effect by:

$$\hat{u}=E(u|\text{"data"}),$$

wherein the appropriate estimator is:

$$\hat{u} = \frac{\int u * p(\text{data} \mid u) p(u) du}{\int p(\text{data} \mid u) p(u) du}$$

wherein:
1. p(data|u) is a likelihood; and
2. p(u) is a prior distribution of QTL effects.

Accordingly, the estimator of the QTL effects depends on the prior distribution of QTL effects. Since we typically test for a QTL at many positions (e.g. 10,000 SNPs), we expect that there is no QTL at most of those positions. Therefore, the prior distribution p(u) must have a high probability for p(0) for the trait in question. For example, milk production traits in dairy cattle are estimated as being determined by at least about 150 QTLs and the distribution of their effects is estimated to be approximately exponential.

Alternatively, a least squares method is employed to estimate the effect of each QTL on a trait. Least squares estimates correspond to assuming a prior distribution of QTL effects with an infinitely large variance. Using least squares, only a QTL with large effect will be detected and used, and thus not all of the genetic variance will be captured by the markers. By assuming that the QTL effects are drawn from normal distribution with constant variance across chromosome segments, a BLUP estimate is derived wherein all effects are estimated simultaneously thereby deriving estimates that are better correlated with the true BVs. However, a Bayesian analysis that uses a more appropriate prior distribution of QTL effects is preferred. For situations where most 'QTLs' have zero effect, least squares and BLUP result in these zero effects being estimated to be small but non-zero and their cumulative effect adding noise to the estimates.

Better estimates are obtained where many possible QTLs are estimated to have zero effect or, equivalently, excluded from the model. If all the QTL effects were from a reflected exponential distribution (i.e. without extra weight at zero), an estimator called the LASSO is preferred (Tibshirani et al., *J. Royal Stat. Soc. Ser. B* 58, 267-288, 1996). However, in the situation where many true effects are zero, LASSO still estimates too many non-zero effects. A pragmatic alternative is to exclude from the model all but the most highly significant effects e.g., by setting a significance threshold so that only one false positive per genome is expected to provide an EBV highly correlated with BV. However, if the effects of these significant QTL are estimated by least squares, the effects will still be overestimated and may require correction by using cross validation e.g., as described by Whittaker et al., *Genet. Res.* 69, 137-144, (1997). This involves estimating the effects in two independent parts of the data, and calculating the regression of one set of solutions on the other. The solutions are then regressed back by this regression coefficient to give unbiased estimates. Cross validation can also be used to choose between competing models. Within a dataset adding extra QTLs increases the accuracy of prediction but the accuracy of GEBVs in an independent dataset can be used to judge whether the accuracy has actually increased.

Preferably, an explicit prior is employed wherein it is assumed that QTL effects are drawn from a normal distribution but that the variance of that distribution varies between QTLs, and that the distribution of variances follows an inverted chi-square distribution. An advantage of using the explicit prior is that the estimates of the biggest or most significant QTLs are not overestimated. This means that the effects can be estimated from all available data regardless of whether the data was part of that used to discover the QTL or not. This provides an important advantage as genomic selection becomes implemented in industry and it becomes impossible to clearly distinguish between discovery data (where least squares estimates are biased) and independent, validation data (where they are unbiased).

In all of the above methods to estimate BV, a polygenic term can be added to the model to account for the genetic variance not explained by the markers. When one marker at a time is tested for significance, omission of the polygenic term from the model produces about twice as many false positives occur as indicated by the significance threshold. This is because, within a dataset, all markers and QTLs are correlated through the pedigree relationship among the animals. Consequently, any marker can, by chance, be correlated with a QTL some distance away or even on another chromosome and so appear to have an effect which is actually an artifact of the pedigree structure. Even when all QTLs are fitted simultaneously, it may be desirable to fit a polygenic effect, as this will capture, to some extent, those QTL that are not associated with markers or haplotypes at high levels of $r^2$.

Preferably, large numbers of animals with marker genotypes and phenotypes are employed to estimate QTL effects, preferably about 2000 records or a greater number.

Database Construction

It will be apparent from the description herein that the present invention provides for the storage of information pertaining to several parameters produced by or used in performance of the invention genotyping and selection methods in the form of one or more databases. Exemplary databases comprise data selected from the group consisting of:

(i) estimated breeding values for one or more individuals of a population e.g., a population having a small effective population size;
(ii) data on ancestors for individuals;
(iii) data on chromosome segments for individuals in the current population;
(iv) data on chromosome segments for ancestors of individuals in the current population;
(v) data on marker genotype(s) in chromosome segment(s) for individuals, e.g., data on marker genotype(s) of one or more ancestors from one or more minimum sets of ancestors each of which is representative of a population having a small effective population size wherein the marker genotypes are arrayed in linkage groups, and/or data on marker genotype(s) of one or more individuals of a population having a small effective population size and one or more minimum sets of ancestors representative of the one or more individuals and optionally the lineages between the marker of the one or more individuals and the ancestors, wherein the marker genotypes are optionally arrayed in linkage groups;
(vi) data on marker genotype(s) in chromosome segment(s) for ancestors;
(vii) data on lineages between the marker genotype(s) and/or chromosome segment(s);
(viii) data on reproductive or regenerative material obtained by performing a process of the invention according to any embodiment described herein;
(ix) data on pedigree and phenotype e.g., obtained from one or more record(s) of pedigree and/or phenotype; and
(x) combinations of any two or more of (i) through (ix).

Preferably, a database of the present invention comprises information regarding the location and nucleotide occurrences of genetic markers e.g, SNPs for significant ancestors or breeding individuals in a population and, more preferably, information pertaining to genetic markers used in the high-throughput system of the present invention or data pertaining to sufficient markers to be representative of a genome of a population i.e., spanning the genome and comprising sufficient polymorphisms to be useful for genome-wide screening. The data may be arrayed in linkage groups, optionally according to a chromosome segment with which they are in linkage disequilibrium.

Information regarding genomic location of a marker can be provided for example by including sequence information of consecutive sequences surrounding a polymorphism, or by providing a position number for the polymorphism with respect to an available sequence entry, such as a Genbank sequence entry, or a sequence entry for a private database, or a commercially-licensed database of DNA sequences. The database can also include information regarding nucleotide occurrences of polymorphic markers.

A database of the present invention can include other information regarding markers or haplotypes, such as information regarding frequency of occurrence in a population.

A database can be divided into multiple parts, wherein each part comprises information that is different in nature e.g., one part for each of (i) through (ix) supra or alternatively, one part for storing sequence data and another part for storing information regarding the sequences e.g., data pertaining to the ancestor founder or individual from which the sequence is derived.

A database may also contain records representing additional information about a marker, for example information identifying the genome in which a particular marker is found, or nucleotide occurrence frequency data, or characteristics of a library or clone or individual which generated the DNA sequence, or the relationship of the sequence surrounding a polymorphic marker to similar DNA sequences in other species.

A database of the present invention can be a flat file database or a relational database or an object-oriented database. The database can be internal i.e., a private database not accessible to external users, and typically maintained behind a firewall, by an enterprise. Alternatively, the database can be external i.e., accessible to external users by virtue of being located outside an internal database, and typically maintained by a different entity than an internal database.

A number of external public biological sequence databases, particularly SNP databases, are available and can be used with the current invention. For example, the dbSNP database available from the National Center for Biological Information (NCBI), part of the National Library of Medicine, USA can be used with the current invention to provide comparative genomic information to assist in identifying SNPs from a wide variety of different breeding populations.

In a further example, the database comprises a population of information that can be modified by users to include new information e.g., actual breeding values from artificial selection or breeding programs, newly-identified markers, haplotypes, traits, chromosome segments, and their associations. The population of information is typically included within a database, and can be identified using the methods of the current invention. For example, a population of information can include all of the SNPs and/or haplotypes of a genome-wide SNP map for a particular set of ancestors and/or individuals in a population having a small effective population size.

Computer System

A computer system of the present invention comprises a database as described herein and a user interface capable of receiving entry of data e.g., for querying the database and displaying results of a database query. The interface may also permit population of one or more fields of data in the database where a user has authority to populate information. The interface can be a graphic user interface where entries and selections are made e.g., using a series of menus, dialog boxes, and/or selectable buttons. The interface typically takes a user through a series of screens beginning with a main menu. The user interface can include links to access additional information, including information from other external or internal databases.

A computer system of the present invention that processes input data and displays the results of a database query will typically comprise a processing unit that executes a computer program, such as, for example, a computer program comprising a computer-readable program code embodied on a computer-usable medium and present in a memory function connected to the processing unit. The memory function can be ROM or RAM. The computer program is typically read and executed by the processing unit. The computer-readable program code relates to a plurality of data files stored in a database.

For example, the computer program can also comprise a computer-readable program code for providing a user interface capable of allowing a user to input nucleotide occurrences of the series of SNPs, locating data corresponding to the entered query information, and displaying the data corresponding to the entered query.

Data corresponding to the entered query information is typically located by querying a database as described above.

In another example, the computer system and computer program are used to perform a method of the present invention, such as a method for estimating the breeding value of an individual.

A computer system of the present invention can be a stand-alone computer, a conventional network system including a client/server environment and one or more database servers, and/or a handheld device. A number of conventional network systems, including a local area network (LAN) or a wide area network (WAN), are known in the art. Additionally, client/server environments, database servers, and networks are well documented in the technical, trade, and patent literature. For example, the database server can run on an operating system such as UNIX, running a relational database management system, a World Wide Web application, and a World Wide Web Server. When the computer system is a handheld device it can be a personal digital assistant (PDA) or another type of handheld device, of which many are known.

The present invention is further described with reference to the following non-limiting example.

EXAMPLE 1

Model Artificial Selection Method for a Holstein Cattle Population

Rationale

Many breeds of livestock have a small effective population size of 50-100, including the Holstein cattle population. This means that most chromosome segments found in animals of the current generation trace back to one of less than about 100 key ancestors within a few generations. This short coalescence time means that the chromosome segments are large and could be recognised by their haplotype at a group of markers. Consequently we can carry out 'in silico' genotyping as follows:
1. Genotyping key ancestors for a dense set of markers;
2. Genotyping individuals of the current population/generation for sufficient markers to permit chromosome segments to be matched to the segments carried by the key ancestors; and
3. Inferring genotypes of individuals in the current population/generation to be the same as those of the key ancestor or founder for the matching chromosome segment.

By this means, it is possible to genotype large numbers of individual in the current population for a moderate number of markers, albeit by obtaining in silico genotypes for a large number of markers. As the cost of genome (re)sequencing drops, this in silico genotyping is extendible to in silico sequencing. That is, the key ancestors are sequenced and then the full genome sequence is imputed for chromosome segments in current animals that match the chromosome segment in key ancestors.

The in silica genotyping and sequencing of the present invention makes use of the known relationships between individual of the current population and the key ancestors thereby reducing the number of markers that must be genotyped on the individuals of the current population.

This method reduces the cost of genomic selection by reducing the number of markers needed to be typed on selection candidates. The method also identifies the causal polymorphisms underlying QTL. If each QTL is attacked separately, the genome sequencing is targeted to a particular region. However, since there are so many QTL affecting many traits of interest, this is a very inefficient approach and it is therefore desirable to perform complete genome (re) sequencing and search for many QTL simultaneously. By performing the in silico methods of the present invention, it will be possible to infer the sequences of thousands of genomes within 5 years e.g., by genotyping a large sample of animals that had been recorded for many traits of interest (eg disease traits) for a moderate number of markers, sequencing the genomes of the key ancestors, tracing the chromosome segments of the individuals of the current population back to their ancestors, inferring the full genome sequence on each animal, and performing genome-wide analysis of sequence (GWAS) based on the inferred full genome sequence. Proceeding on this basis, the method fo the present invention is useful for identifying large numbers of mutations affecting disease susceptibility or other traits.

Methods and Results

The present invention provides a method of artificial selection comprising:
1. Identifying the minimum set of key ancestors that represent most of the chromosome segments in a current population;
2. Genotyping the key ancestors for a dense set of markers;
3. Genotyping one or more individuals of a current population for sufficient markers to thereby permit chromosome segments to be matched to the segments carried by the key ancestors;
4. Tracing the chromosome segments of the one or more individuals of the current population cattle to a key ancestor;
5. Inferring the genotypes of markers within one or more chromosome segments of the one or more individuals in the current population to be the same as those of the key ancestor; and
6. Using the inferred genotype of the one more individuals in the current population to estimate the breeding value of said one or more individuals.

These steps are described in more detail with reference to the artificial selection of Holstein cattle.

1. Identifying the Minimum Set of Key Ancestors that Represent Most of the Chromosome Segments in a Current Population Key ancestors for a population of Holstein cattle are determined e.g., based on known pedigrees and/or by estimating the relationships between animals from DNA marker linkage analysis. The estimation of key ancestors based upon DNA markers provides a more accurate estimate of relationships between animals than the 'known' pedigree which is often incomplete and contains errors. Preferably, an A matrix estimated from the DNA markers, and/or the pedigree-derived A matrix is used to identify the key ancestors.

By using the additive relationship matrix (A) described herein above the key ancestors provided in Tables 2 and 3 were obtained for a population of 2300 Holstein cattle.

2. Genotyping the Key Ancestors for a Dense Set of Markers

As we did not have genotypes on the key ancestors of the Holstein cattle population under study, we modelled the ancestor population using a founder population of 425 animals without sire and dam both known. In practice, fewer key ancestors would be needed than this because either more complete pedigrees are available or relationships are more readily deduced from the marker data.

We then inferred the genotypes of the founders based on genotypes of their relatives for 11 microsatellite markers spanning 2.9 cM of chromosome 21, using a Markov Chain Monte Carlo (MCMC) method described originally by Schafer, J. L. (1997), Analysis of Incomplete Multivariate Data, New York: Chapman and Hall. In this approach, the genotype of each animal is sampled from a posterior distribution conditional on the genotypes of parents, grandparents, offspring, grand offspring and mates. One sample from the posterior distribution of genotypes was used and the inferred genotypes on the founder animals were then deemed to be the actual genotypes.

Preferably, the dataset of genotypes from ancestors listed in Table 2 or 3 would be derived for a dense set of markers by standard genotyping approaches using semen as a source of genetic material for the genotyping and/or based on available genotype data, and optionally combined with an MCMC method to infer or impute the missing values.

3. Genotyping One or More Individuals of a Current Population for Sufficient Markers to Thereby Permit Chromosome Segments to be Matched to the Segments Carried by the Key Ancestors We used a dataset of 2300 Holstein cattle that had been genotyped for up to 11 microsatellite markers spanning 2.9 cM of chromosome 21. Ten of these markers were treated as the markers that have been genotyped on the current population and on the founders. The remaining (11th) marker was treated as a marker that had been genotypes only on the founder population, along with other unknown markers that are genotyped only on founders. We reasoned that this was sufficient to rigorously test the method of the invention, because this 11th marker has five (5) almost equally-common alleles and, as a consequence, represented a difficult marker at which to predict a genotype. Genotypes at other markers, such as SNPs, would be easier to predict than the example provided herein.

To test the accuracy of the method of the invention in this model system, we then defined a subset of "selection candidates" from the current population as those animals having no progeny but with a known sire and dam. The selection candidates had been genotyped at the 11th marker in the 2.9 cM region of chromosome 21, however that known marker genotype was then masked or hidden from the analysis, such that the selection candidates were assumed to be known for a maximum of only 10 microsatellite markers in this region of the chromosome. Such a blind analysis of the markers for the selection candidates was performed to permit us to compare the true marker genotype with the marker genotype predicted by the analysis i.e., when the missing value was hidden.

4. Tracing the Chromosome Segments of the One or More Individuals of the Current Population Cattle to a Key Ancestor In the model system, because a specific segment of chromosome 21 was employed to model the accuracy of the method, it was not strictly necessary to trace the chromosome segments of the selection candidates back to a key ancestor.

Notwithstanding this limitation, we compared the genotypes of the selection candidates within the 2.9 cM region of chromosome 21 for a limited subset of markers for which they had been genotypes to the inferred the genotypes of the founders in the same chromosome region and aligned the markers to thereby trace the chromosome segments of the one or more individuals of the current population cattle to a particular founder.

The chromosome segments were traced through the pedigree from the selection candidates to the founders based on the 10 markers using the same MCMC program as above.

5. Inferring the Genotypes of Markers within One or More Chromosome Segments of the One or More Individuals in the Current Population to be the Same as Those of the Key Ancestor The missing i.e., hidden genotype on the selection candidates were inferred by the MCMC program because it traces the origin of each chromosome position in a selection candidate back to one of the founders on which the 11th marker genotype was known. In 96% of cases the predicted genotype agreed with the true genotype. Data are available on request.

In this example, the marker genotypes of the founders were actually inferred from genotypes of relatives, but ideally they would be known. They were inferred from relatives in this example because DNA for genotyping the founders was not available. Thus, we tested the method under unfavourable conditions and conclude that in more favourable conditions where the genotypes of the founders or ancestors are known, the method would deliver results that are equal to those of the present example or better.

A number of other analytical methods could be employed to infer the missing genotypes of the selection candidates e.g. a pedigree-based peeling algorithm including multiple iterative peeling such as that described by Meuwissen et al., *Genetics* 161, 373-379, 2002).

Alternatively, or in addition, a method designed for unrelated animals eg using the fastPHASE algorithm available from University of Washington, Ann Arbor, Mich. 48109-2029, USA. The fastPHASE algorithm implements methods for estimating haplotypes and missing genotypes from population SNP genotype data. When used on related animals, fastPHASE recognizes common haplotypes derived from key ancestors. For example, we have also tested the accuracy of fastPHASE in the inventive method, using the same dataset as above. We analysed a dataset from 680 animals for which 6 or more out of the 11 marker genotypes were known. One-half these animals were used as an experimental set and one-half were selection candidates. The genotype at marker 5 was hidden from the fastPHASE analysis. In this variation, 91% of missing genotypes were predicted correctly using fastPHASE.

The present invention also encompasses the use of two steps to infer genotypes on selection candidates from those in key ancestors. For example, 100 key ancestors can be genotyped for all known markers (eg 1,000,000 markers), or fully sequenced. All males used for breeding or all stud males used for breeding can be separately genotyped for a subset of the known markers e.g., 50,000 markers, and the selection candidates genotyped for fewer markers e.g., only 2000 markers. The chromosome segments in the selection candidates can be traced over one or a few generations to the breeding males and they can be traced to the key ancestors.

This makes use of high throughput genotyping (50,000 markers) on a small fraction of the total population.

6. Using the Inferred Genotype of the One More Individuals in the Current Population to Estimate the Breeding Value of Said One or More Individuals.

Standard methods as described herein are used to predict breeding value of the selection candidate from the inferred genotypes of the markers. These all use an equation that predicts BV from marker genotypes that is derived from the analysis of a sample of animals that have both genotypes and either estimated breeding values (EBVs) or phenotypic records. A preferred method described herein calculates the expected value of the BV conditional on the marker genotypes and on a prior distribution of the effects of genes on the trait of interest. Methods for estimating this prior distribution are publicly available.

CONCLUSIONS

The model described herein for a population of Holstein cattle is readily extrapolated and applicable to whole genome studies employing ancestors as opposed to founders. In the method of the invention a group of key ancestors would be genotyped for many markers; selection candidates would be genotyped for a smaller number of markers; the chromosome segments of the selection candidates would be traced back to those of the key ancestors and this would allow all the marker genotypes known on the key ancestors to be imputed for the selection candidates. In the exemplification provided herein, we treated all the animals with known genotypes for up to 11 markers as the selection candidates, and then traced the known pedigree of these animals as far as possible to identify 425 founders that did not have two known parents. These 425 founders thus are truly representative of key ancestors in this example. This is a larger number of key ancestors than normal, however the larger size of the founder population is a consequence of incomplete pedigree data and poor genotype data for the ancestors shown in Tables 2 and 3. Ten of the markers were considered equivalent to the small number of markers typed on selection candidates. One of those markers was treated as an example of the many markers typed on the key ancestors that we desire to impute on the selection candidates. Because the key ancestors have not been genotyped for the 11 markers, we employed MCMC modelling to deduce the marker genotypes of the 425 founders. We then ran the MCMC program again with the 11$^{th}$ marker genotype deleted on the selection candidates and used the MCMC program to impute the missing genotype. We inferred only one missing genotype but it is a typical example because, had the founders been genotyped for 110 markers it would have been possible to infer the missing 100 markers as accurately as the one marker actually inferred by iteration of the process. For example, the method can be tested on an additional dataset from the genotypes of about 700 Holstein bulls for 50,000 SNP markers using an Illumina assay, which form the selection candidates, from which data on all but about 2000 SNPs are hidden or masked; and the genotypes of key ancestors of these bulls determined and used to impute/infer the missing 48,000 genotypes on the selection candidates.

We expect the method of the invention to perform better than in this model because, in our model the need to infer the genotypes of key ancestors from those of their relatives means that the genotypes on key ancestors may contain some errors. In an ideal application the pedigree would be known and/or genotypes on the key ancestors would be known, thereby permitting selection candidates to be traced back to a smaller number of key ancestors. Thus, the exemplification herein demonstrates that the method will work even in an unfavourable situation where the genotypes of key ancestors have to be inferred from those of their relatives.

We claim:

1. A method of selective breeding in a non-human population having a genetic diversity equivalent to an effective population size (Ne) of less than 1000, said method comprising:
   (i) detecting, in nucleic acids isolated from more than one chromosome segment of a plurality of individuals in the non-human population, the presence or absence of more than one set of informative markers, wherein each set of informative markers is a set of informative markers at a gene or locus associated with a heritable trait on a chromosome segment, to thereby determine the genotype of each individual at each set of such informative markers, and wherein each set of informative markers is a set of known informative markers and wherein for each set of informative markers, the genotype at one or more other known informative markers at the gene or locus associated with the heritable trait is not determined;
   (ii) for each individual, comparing the genotype at each set of informative markers determined in step (i) to the genotype at each such set of informative markers in an ancestor and/or founder contributing at least 0.1% of the total genetic variance to the current population to thereby determine the lineage of each of the chromosome segments of the individual from an ancestor and/or founder of the population from which each of the chromosome segments are derived, wherein the genotype of the ancestor and/or founder is known for each of the more than one set of informative markers detected in each individual of step (i) as well as for at least one of the one or more other known informative markers of each set for which the genotype(s) was/were not determined for each individual in step (i);
   (iii) for each individual, inferring that the genotype at the one or more other known informative markers of each set for which the genotype(s) was/were not determined in step (i) is the same as for the ancestor and/or founder based on the lineage of the chromosome segments determined at (ii) to thereby produce one or more inferred genotype(s) for each set of informative markers;
   (iv) estimating the breeding value of each individual based on genotypes comprising the one or more inferred genotype(s) determined in step (iii) to produce an estimated breeding value (EBV) for each said individual;
   (v) selecting from the plurality of individuals, an individual having a high EBV;
   (vi) obtaining reproductive or regenerative material from the individual selected, and
   (vii) producing one or more individuals or one or more generations of individuals from the reproductive or regenerative material, thereby selectively breeding in the non-human population.

2. The method of claim 1, wherein the one or more gene or locus associated with a heritable trait is a single gene locus.

3. The method of claim 1, wherein the one or more gene or locus associated with a heritable trait is a Quantitative Trait Locus (QTL).

4. The method according claim 1, wherein the population is a population of animals.

5. The method according to claim 4, wherein the population is a population of animals selected from cattle, sheep, pigs, poultry, fish and crustaceans.

6. The method according to claim 5, wherein the cattle are Holstein cattle.

7. The method according to claim 1, wherein the informative markers of the more than one set of informative markers are selected from: an allele, haplotype, haplogroup, locus, quantitative trait locus, polymorphism, STR and combinations thereof.

8. The method according to claim 7, wherein the informative markers of the more than one set of informative markers comprise a polymorphism and the polymorphism is a single nucleotide polymorphism (SNP).

9. The method of claim 7, wherein the informative markers of the more than one set of informative markers comprise a STR and the STR is a microsatellite.

10. The method of claim 1, wherein detecting the presence or absence of more than one set of informative markers comprises hybridizing a probe or primer selectively to nucleic acid comprising a marker and detecting the hybridized probe or primer.

11. The method of claim 10 wherein detecting the presence or absence of more than one set of informative markers comprises performing a primer extension reaction or an amplification reaction.

12. The method according to claim 1, wherein the ancestor and/or founder contributing at least 0.1% of the total genetic variance to the current population has a genome sequence which is known, and wherein inferring the genotype at the one or more other known informative markers of each set for which the genotype(s) was/were not determined in step (i) to be the same as for an ancestor/founder comprises inferring genome sequences of the individual in the current population based on the genome sequence of the ancestor and/or founder.

13. The method of claim 1, wherein the genotype of the ancestor and/or founder is known for all the known informative marker(s) of each set for which genotype information was/were not determined in step (i).

14. The method of claim 1, wherein each ancestor and/or founder provides at least 0.5% of the total genetic variance to the current population.

15. The method of claim 14, wherein each ancestor and/or founder provides at least 1% of the total genetic variance to the current population.

16. The method of claim 1, further comprising determining ancestors and/or founders representative of the total genetic variance of the current population for use in inferring the missing genotypes, by performing a process comprising:
   (i) selecting an ancestor or founder contributing the highest proportion of genes to the current population;
   (ii) selecting an ancestor or founder that provides the highest marginal contribution of genes compared to the ancestor at (i);
   (iii) conducting sufficient iterations of (ii) to describe the variance in the current population; and
   (iv) assembling the selected ancestors describing the variance in the current population as ancestors and/or founders that are representative of the genetic variance of the current population.

* * * * * the present invention provides methods for estimating the breeding value of individuals in populations such as those having small effective population size (Ne) e.g., to identify selection candidates having high breeding values, wherein the methods comprise inferring one or more genotypes for one or more markers at a locus or QTL to be the same as for an ancestor or founder or a subset of ancestors and/or founders from which a corresponding chromosome segment is derived and estimating the breeding value of the individual based on the inferred genotype(s).

(12) EX PARTE REEXAMINATION CERTIFICATE (11973rd)
United States Patent
Hayes et al.

(10) Number: US 10,179,938 C1
(45) Certificate Issued: Dec. 28, 2021

(54) ARTIFICIAL SELECTION METHOD AND REAGENTS

(71) Applicant: Agriculture Victoria Services Pty Limited, Attwood (AU)

(72) Inventors: Ben Hayes, Kensington (AU); Michael Goddard, Diamond Creek (AU)

Reexamination Request:
No. 90/014,582, Sep. 21, 2020

Reexamination Certificate for:
Patent No.: 10,179,938
Issued: Jan. 15, 2019
Appl. No.: 14/245,334
Filed: Apr. 4, 2014

Related U.S. Application Data

(63) Continuation of application No. 12/448,463, filed as application No. PCT/AU2007/002006 on Dec. 21, 2007, now abandoned.

(60) Provisional application No. 60/876,623, filed on Dec. 21, 2006.

(51) Int. Cl.
*C12Q 1/68* (2018.01)
*C12Q 1/6888* (2018.01)
*A01K 67/02* (2006.01)

(52) U.S. Cl.
CPC ............ *C12Q 1/6888* (2013.01); *A01K 67/02* (2013.01); *C12Q 1/68* (2013.01)

(58) Field of Classification Search
None
See application file for complete search history.

(56) References Cited

To view the complete listing of prior art documents cited during the proceeding for Reexamination Control Number 90/014,582, please refer to the USPTO's public Patent Application Information Retrieval (PAIR) system under the Display References tab.

*Primary Examiner* — Sharon Turner

(57) ABSTRACT

The present invention provides methods for estimating the breeding value of individuals in populations such as those having small effective population size (Ne) e.g., to identify selection candidates having high breeding values, wherein the methods comprise inferring one or more genotypes for one or more markers at a locus or QTL to be the same as for an ancestor or founder or a subset of ancestors and/or founders from which a corresponding chromosome segment is derived and estimating the breeding value of the individual based on the inferred genotype(s).

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-16 are cancelled.

\* \* \* \* \*